(12) United States Patent
Ren

(10) Patent No.: US 12,159,419 B2
(45) Date of Patent: Dec. 3, 2024

(54) MOTION DETECTION FOR INTERNAL BREAST TISSUE IN TOMOSYNTHESIS

(71) Applicant: HOLOGIC, INC., Marlborough, MA (US)

(72) Inventor: Baorui Ren, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 304 days.

(21) Appl. No.: 17/763,781

(22) PCT Filed: Aug. 31, 2020

(86) PCT No.: PCT/US2020/048762
§ 371 (c)(1),
(2) Date: Mar. 25, 2022

(87) PCT Pub. No.: WO2021/061346
PCT Pub. Date: Apr. 1, 2021

(65) Prior Publication Data
US 2022/0343513 A1 Oct. 27, 2022

Related U.S. Application Data

(60) Provisional application No. 62/907,079, filed on Sep. 27, 2019.

(51) Int. Cl.
*G06T 7/246* (2017.01)
*A61B 6/02* (2006.01)
(Continued)

(52) U.S. Cl.
CPC .............. *G06T 7/248* (2017.01); *A61B 6/025* (2013.01); *A61B 6/0414* (2013.01); *A61B 6/502* (2013.01);
(Continued)

(58) Field of Classification Search
CPC ....... A61B 6/025; A61B 6/0414; A61B 6/502; A61B 6/5264; G06T 2207/30068;
(Continued)

(56) References Cited

U.S. PATENT DOCUMENTS 9,235,888 B2 * 1/2016 Jerebko ................... G06T 3/18
2004/0094167 A1 * 5/2004 Brady ...................... G06T 7/55
600/443

(Continued)

FOREIGN PATENT DOCUMENTS

JP 2012-35068 A 2/2012
JP 2019-103944 6/2019
(Continued)

OTHER PUBLICATIONS

International Search Report and Written Opinion of the International Searching Authority for International Patent Application No. PCT/US2020/048762 mailed Nov. 30, 2020, 17 pages.

(Continued)

*Primary Examiner* — Dani Fox
*Assistant Examiner* — Soorena Kefayati
(74) *Attorney, Agent, or Firm* — Merchant & Gould P.C.

(57) ABSTRACT

Methods and systems for identifying internal motion of a breast of a patient during an imaging procedure. The method may include compressing the breast of the patient in a mediolateral oblique (MLO) position. During compression of the breast, a first tomosynthesis MLO projection frame for a first angle with respect the breast is acquired and a second tomosynthesis MLO projection frame for a second angle with respect to the breast is acquired. Boundaries of the pectoral muscle are identified in the projection frames and boundary representations are generated. A difference between the first representation and the second representation is determined. A motion score is then generated based (Continued)

on at least the difference between the first representation and the second representation.

21 Claims, 16 Drawing Sheets

(51) Int. Cl.
*A61B 6/04* (2006.01)
*A61B 6/50* (2024.01)
*G06T 7/00* (2017.01)

(52) U.S. Cl.
CPC .. *G06T 7/0016* (2013.01); *G06T 2207/10112* (2013.01); *G06T 2207/10116* (2013.01); *G06T 2207/30068* (2013.01)

(58) Field of Classification Search
CPC . G06T 2207/10116; G06T 2207/10112; G06T 7/246; G06T 7/0016; G06T 7/248; G06T 7/20; G06T 7/251; G06T 7/254
See application file for complete search history.

(56) References Cited

U.S. PATENT DOCUMENTS

| | | | | |
|---|---|---|---|---|
| 2009/0123052 A1* | 5/2009 | Ruth | ............ | A61B 6/025 382/132 |
| 2010/0329514 A1* | 12/2010 | Mundry | ............ | G06T 7/254 382/107 |
| 2012/0033868 A1* | 2/2012 | Ren | ............ | A61B 6/502 378/21 |
| 2012/0189175 A1* | 7/2012 | Highnam | ............ | G06T 7/0012 382/128 |
| 2015/0010219 A1* | 1/2015 | Behiels | ............ | G06T 7/12 382/128 |
| 2015/0332485 A1* | 11/2015 | Klausz | ............ | A61B 6/025 378/8 |
| 2015/0342549 A1* | 12/2015 | Kwon | ............ | A61B 6/469 378/37 |
| 2016/0133033 A1* | 5/2016 | Highnam | ............ | G06T 11/008 382/131 |
| 2017/0132792 A1* | 5/2017 | Jerebko | ............ | G16H 50/30 |
| 2018/0046875 A1* | 2/2018 | Caluser | ............ | A61B 6/584 |
| 2018/0122067 A1* | 5/2018 | Reicher | ............ | A61B 6/463 |
| 2019/0059841 A1* | 2/2019 | Palma | ............ | G06T 11/008 |
| 2019/0287241 A1* | 9/2019 | Hill | ............ | A61B 6/5282 |
| 2020/0372693 A1* | 11/2020 | Kobayashi | ............ | A61B 6/466 |
| 2021/0097677 A1* | 4/2021 | Highnam | ............ | G16H 50/20 |

FOREIGN PATENT DOCUMENTS

| | | |
|---|---|---|
| WO | 2015/175728 A1 | 11/2015 |
| WO | 2014/203531 | 2/2017 |

OTHER PUBLICATIONS

Ren, B. et al., "Automatic patient motion detection in digital breast tomosynthesis", Medical Imaging 2011: Physics of Medical Imaging, SPIE, 7961(1): 1-12 (Mar. 2011).

PCT International Preliminary Report on Patentability in PCT/US2020/048762, mailed Apr. 7, 2022, 11 pages.

* cited by examiner

MOTION DETECTION FOR INTERNAL BREAST TISSUE IN TOMOSYNTHESIS

CROSS-REFERENCE TO RELATED APPLICATIONS

This application is a National Stage Application of PCT/US2020/048762, filed on Aug. 31, 2020, which claims priority to and the benefit of U.S. Provisional Patent Application Ser. No. 62/907,079, filed on Sep. 27, 2019, the disclosures of which are hereby incorporated herein by reference their entireties. To the extent appropriate, a claim of priority is made to each of the above disclosed applications.

BACKGROUND

X-ray screening exams are used to detect breast cancer and other diseases. Efforts to improve the sensitivity and specificity of breast x-ray systems have led to the development of tomosynthesis systems. Breast tomosynthesis is a three-dimensional imaging technology that involves acquiring images of a stationary compressed breast at multiple angles during a short scan. The individual images are reconstructed into a series of thin, high-resolution slices that can be displayed individually or in a dynamic cine mode. Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

The present technology relates to the detection of internal breast tissue motion during an imaging procedure. In an aspect, the technology relates to a method for identifying internal motion of a breast of a patient during an imaging procedure. The method includes compressing the breast of the patient in a mediolateral oblique (MLO) position; during compression of the breast, acquiring a first tomosynthesis MLO projection frame for a first angle with respect the breast; during compression of the breast, acquiring a second tomosynthesis MLO projection frame for a second angle with respect to the breast; identifying a first boundary of a pectoral muscle in the first projection frame; generating a first representation of the first boundary of the pectoral muscle; identifying a second boundary of the pectoral muscle in the second projection frame; generating a second representation of the second boundary of the pectoral muscle; determining a difference between the first representation and the second representation; and generating a motion score based on at least the difference between the first representation and the second representation.

In an example, the first generated representation is a two-dimensional representation. In another example, the difference is based on an area between the first representation and the second representation. In yet another example, the difference is based on a minimum distance between the first representation and the second representation. In a further example, the method further includes comparing the difference to an expected value, wherein the expected value is based on at least one of: an x-ray angle of an x-ray source for the first projection frame and an x-ray angle of the x-ray source for the second projection frame, or a fitted curve based on at least the first tomosynthesis MLO projection frame and the second tomosynthesis MLO projection frame; and based on the comparison of the difference to the expected value, generating a motion warning. In still another example, the method further includes displaying at least a portion of the first projection frame and the second projection frame in a cine view concurrently with a plurality of parallel motion guides.

In another example, the method further includes receiving a selection of one of the plurality of the parallel motion guides; receiving an input to move the selected parallel motion guide to a new location; and based on the received input to move the selected parallel motion guide, displaying the selected parallel motion guide in the new location. In yet another example, the plurality of parallel motion guides are evenly spaced relative to one another.

In another aspect, the technology relates to a method for identifying internal motion of a breast of a patient during an imaging procedure. The method includes compressing the breast of the patient in a mediolateral oblique (MLO) position; acquiring a plurality of tomosynthesis MLO projection frames during the compressing of the breast, wherein the plurality of tomosynthesis MLO projection frames include an image of a portion of the breast and a portion of a pectoral muscle of the patient; for at least two of the plurality of the tomosynthesis MLO projection frames, identifying a boundary of the pectoral muscle; for the at least two of the plurality of the tomosynthesis MLO projection frames, generating a representation for the boundary of the pectoral muscle; determining a first difference between the generated representations for the at least two of the plurality of the tomosynthesis MLO projection frames; determining a second difference between the first difference and an expected value for the first difference; comparing the second difference to a predetermined threshold; and based on the comparison of the second difference to the predetermined threshold, generating a motion warning.

In an example, the generated representation is a two-dimensional representation. In another example, the first difference is based on an area between the generated representations. In yet another example, the first difference is based on a minimum distance between the generated representations. In a further example, the second difference is a shift variance value. In still another example, the method further includes displaying at least a portion of the projection frames consecutively in a cine view concurrently with a plurality of parallel motion guides.

In another example, the method includes receiving a selection of one of the plurality of the parallel motion guides; receiving an input to move the selected parallel motion guide to a new location; and based on the received input to move the selected parallel motion guide, displaying the selected parallel motion guide in the new location. In yet another example, the plurality of parallel motion guides are evenly spaced relative to one another.

In another aspect, the technology relates to a system for identifying internal motion of a breast of a patient during an imaging procedure. The system includes an x-ray source configured to move rotationally around the breast; a compression paddle configured to compress the breast in a mediolateral oblique (MLO) position; and an x-ray detector disposed opposite the compression paddle from the x-ray source. The system further includes at least one processor; and memory storing instructions that, when executed by the at least one processor, cause the system to perform a set of operations. The operations include, during a compression of the breast in the MLO position, emitting, from the x-ray source, a first x-ray emission from the x-ray source at a first angle relative to the breast; detecting, by the x-ray detector, the first x-ray emission from the x-ray source after the first x-ray emission has passed through the breast; emitting, from the x-ray source, a second x-ray emission at a second angle relative to the breast; and detecting, by the x-ray detector, the second x-ray emission after the second x-ray emission has passed through the breast. The method further includes generating, based on the detected first x-ray emission, a first tomosynthesis MLO projection frame for the first angle; generating, based on the detected second x-ray emission, a second tomosynthesis MLO projection frame for the second angle; identifying a first boundary of a pectoral muscle in the first projection frame; generating a first representation of the first boundary of the pectoral muscle; identifying a second boundary of the pectoral muscle in the second projection frame; generating a second representation of the second boundary of the pectoral muscle; determining a difference between the first representation and the second representation; and generating a motion score based on at least the difference between the first representation and the second representation.

In an example, the first generated representation is a two-dimensional representation. In another example, the difference is based on an area between the first representation and the second representation. In yet another example, the difference is based on a minimum distance between the first representation and the second representation.

In another aspect, the technology relates to a method for identifying internal motion of a breast of a patient during an imaging procedure. The method includes compressing the breast of the patient; acquiring a plurality of tomosynthesis projection frames during the compressing of the breast, wherein the plurality of tomosynthesis projection frames include an image of a portion of the breast and a portion of a pectoral muscle of the patient; for at least a subset of the plurality of the tomosynthesis projection frames, identifying a boundary of the pectoral muscle; for the identified boundaries of the pectoral muscle, generating a boundary representation for the identified boundary of the pectoral muscle; measuring a distance between the generated boundary representations for at least a subset of all possible pairs of the boundary representations; determining an expected distance value for each boundary representation for which a distance is measured; based on the measured distance and the expected distance value, determining a shift variance for each boundary pair for which a distance is measured; comparing the shift variance to a predetermined threshold; and based on the comparison of the shift variance to the predetermined threshold, generating a motion warning.

In another aspect, the technology relates to a method for identifying internal motion of a breast of a patient during an imaging procedure. The method includes compressing the breast of the patient; acquiring a plurality of tomosynthesis projection frames during the compressing of the breast, wherein the plurality of tomosynthesis projection frames include an image of a portion of the breast and a portion of a pectoral muscle of the patient; for at least a subset of the plurality of the tomosynthesis projection frames, identifying a boundary of the pectoral muscle; for the identified boundaries of the pectoral muscle, generating a boundary representation for the identified boundary of the pectoral muscle; generating a reference line that intersects the generated boundary representations; identifying a reference point along the reference line; for at least a subset of the generated boundary representations, calculating an intersection distance from the reference point to an intersection point of the respective boundary with the reference line; determining expected intersection distance values based on the calculated intersection distances; determining an intersection shift variance for each of the boundary representations for which an intersection distance is calculated; comparing the intersection shift variance to a predetermined threshold; and based on the comparison of the intersection shift variance to the predetermined threshold, generating a motion warning.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1:
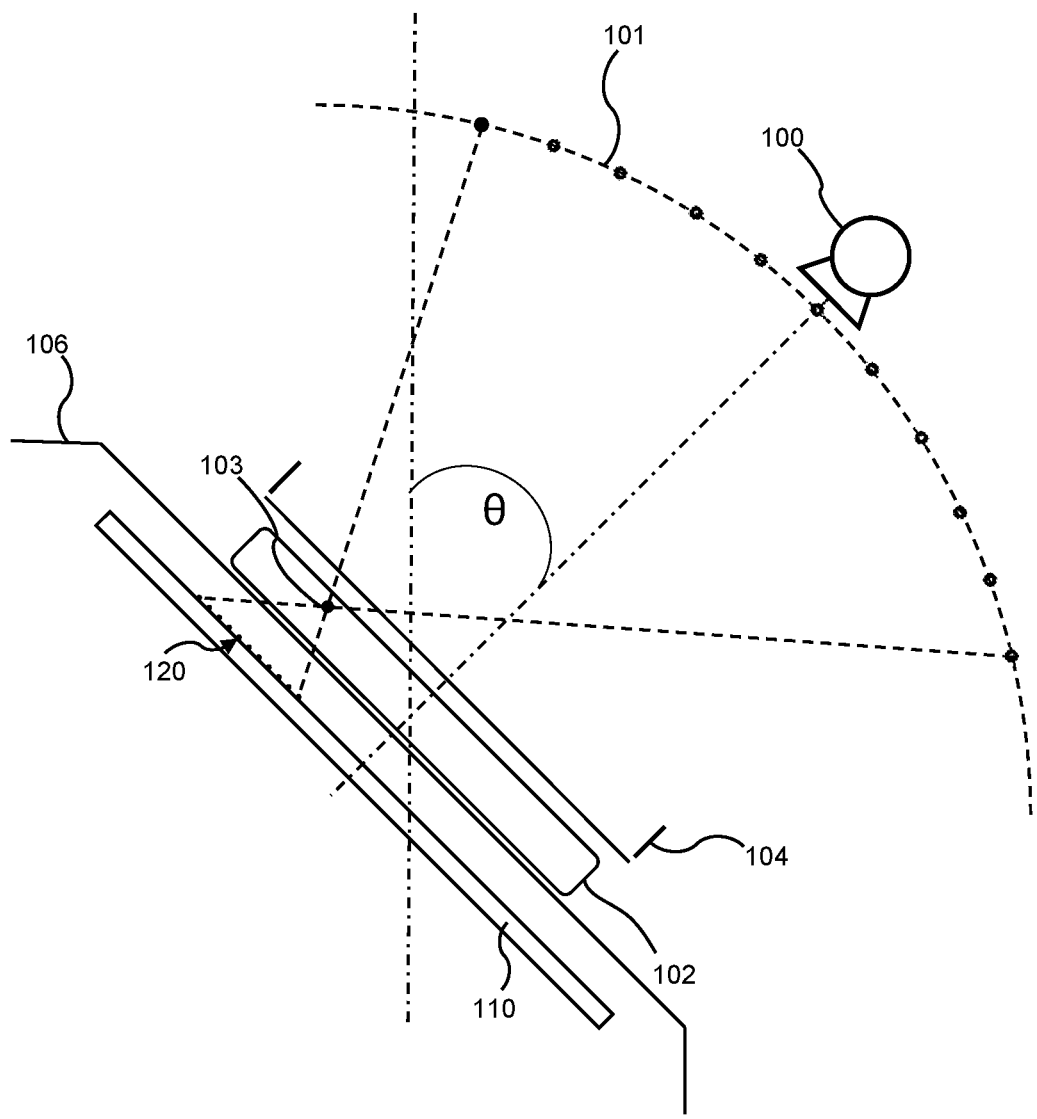
FIG. 1 depicts an example portion of a tomosynthesis system with a breast compressed in a mediolateral oblique (MLO) position.

As discussed above, breast tomosynthesis is a three-dimensional imaging technology that involves acquiring images of a stationary compressed breast at multiple angles during a short scan. The individual images are reconstructed into a series of thin, high-resolution slices. Because multiple images are captured over a period of time and used for a reconstruction, it is possible that the patient may move during a tomosynthesis imaging procedure. Motion during the procedure negatively affects the quality of the resultant reconstruction and tomosynthesis slices. Specifically, patient motion may cause blurring, anatomical distortions, and/or artifacts, which can be exaggerated during longer exposure times. If the patient's motion is substantial, an additional imaging procedure may be required to obtain better quality tomosynthesis images for the patient. Being able to automatically detect motion at or near the conclusion of a tomosynthesis imaging procedure allows for a patient to be re-imaged while the patient is still located at the imaging facility. For example, without automated motion detection technology, patient motion during an imaging procedure would not be identified, if at all, until a physician reviewed a set of medical images and noticed blurring or other indicia of patient motion. Such a review often occurs days if not weeks after an imaging procedure. Accordingly, a patient would have to then return to an imaging facility for additional imaging at a later date. With automatic motion detection, the patient is able to re-imaged almost immediately after the first imaging procedure if there was substantial motion during the first imaging procedure. In addition, the automatic motion detection techniques discussed herein may also provide a score or measure of the detected motion. The measure or score may be further used in motion correction or deduction techniques to improve ultimate image quality.

Some motion detection concepts were discussed in U.S. Pat. No. 9,498,180 (the '180 Patent), which is incorporated herein by reference in its entirety. The '180 Patent discloses techniques for identifying motion of the skin line of the breast. Identification of motion of the skin line has many benefits including the fact that the skin line appears in the most commonly acquired image views—namely craniocaudal (CC) and mediolateral oblique (MLO) views. It has been discovered that, in some situations, motion of the skin line does not accurately reflect motion of the internal breast tissue. That is, in some situations, the skin line may move during the imaging procedure, but the internal breast tissue may remain substantially stationary. The opposite example also occurs where internal breast tissue moves during the imaging procedure, but the skin line remains substantially stationary. Such distinctions matter where lesions or regions of interest occur further away from the skin line and a reviewing physician may need to know whether breast motion occurred near the lesion or not.

To help resolve this problem, a new technique has been developed that approximates the motion of internal breast tissue. More specifically, the present technology examines the location of the pectoral muscle in a plurality of tomosynthesis projection frames. Based on the locations of the pectoral muscle, the presence of motion and the magnitude of such motion can be identified. Due to the location that the pectoral muscle in the projection frames, motion of the pectoral muscle provides a more accurate approximation of motion of the internal tissue of the breast than motion of the skin line. The present technology may also utilize other internal structures of the breast or the patient, such as an implant in the breast or the chest wall muscle of the patient.

The respective downside to some embodiments of the present technology, however, is that some embodiments may only be utilized for a subset of medical image views of the breast. For instance, in images where the pectoral muscle is generally not present, such as the CC view, the present technology may not be able to approximate internal motion of the breast based on the pectoral muscle. For images where the pectoral muscle is present, the present technology provides for an improved approximation of motion of the internal breast tissue. The most common view for which the pectoral muscle is present is the MLO view. To acquire an MLO view, a tomosynthesis gantry is rotated approximately 45 degrees and the patient's breast is compressed at the 45 degree angle. Due to the 45 degree compression, the MLO compression is often more uncomfortable for a patient than other views, such as the CC view. Due to the increased discomfort, the patient is more likely to move during the procedure and the motion is more likely to be substantial. In internal studies, it has been identified that approximately 66% of patient motion occurs during MLO compressions. Accordingly, while some embodiments of the present technology may not be used for all views, the present technology is useful for views where substantial motion is most likely to occur.

FIG. 1 illustrates an example portion of a tomosynthesis system with a breast compressed in a MLO position. The example system includes an x-ray source 100 that moves along an arc 101, a compression paddle 104, a breast platform 106, and an x-ray detector or receptor 110. During a tomosynthesis scan, a patient's breast 102 is immobilized and compressed between the compression paddle 104 and the breast platform 106. The x-ray receptor 110 is disposed within a housing located below the breast platform 106. The x-ray receptor 110 receives and/or detects the x-rays emitted from the x-ray source 100 after the x-rays have passed through the breast 102. The x-ray source 100 moves along an arc 101 which may be centered on the top surface of the receptor 110. At predetermined discrete positions source 100 is energized to emit a collimated x-ray beam, for example and without limitation, at every 1.07° of an arc of ±7.5°. The beam irradiates the breast 102, and radiation that has passed through the breast is received by receptor 110. Receptor 110 and associated electronics generate image data in digital form for each pixel of a rectangular grid of pixels at each predetermined discrete angular position of source 100. In the MLO position, the breast is compressed at approximately a 45 degree angle (θ) from vertical. In some examples, the compression may be between approximately 40-60 degrees.

The motion of source 100 may be continuous or discontinuous. If motion is continuous, a respective set of image data is accumulated over a small increment of continuous motion, e.g., a 0.1° to 0.5° arc of motion of source 100, although these non-limiting parameters are only an example. Different ranges of motion of the source 100 can be used, and the motion of the source 100 may be along an arc centered at a different axis, such as inside immobilized breast 102 or at breast platform 106 or at receptor 110. Furthermore, source motion is not necessarily along an arc, and can be translational or a combination of different types of motions, such as partly translational and partly rotational. In some examples, x-rays may be emitted between −7.5° and 7.5° from the center point of the arc, and 15 different projection frames may be obtained from a single tomosynthesis imaging procedure.

A distinct feature 103 of the breast will project onto the detector at a different position for each different image, resulting in a projection path 120, because the x-ray source position is different for each image. Furthermore, the projection path 120 among all view angles generally follows a smooth trajectory for a tomosynthesis scan which is free of patient motion because of the way x-ray source motion is defined, e.g., in a controlled arc, and because x-ray exposures are taken in a temporally and spatially uniform manner. However, the projection of the feature will not follow a smooth trajectory if the patient moves during the scan.

Figure 2A:
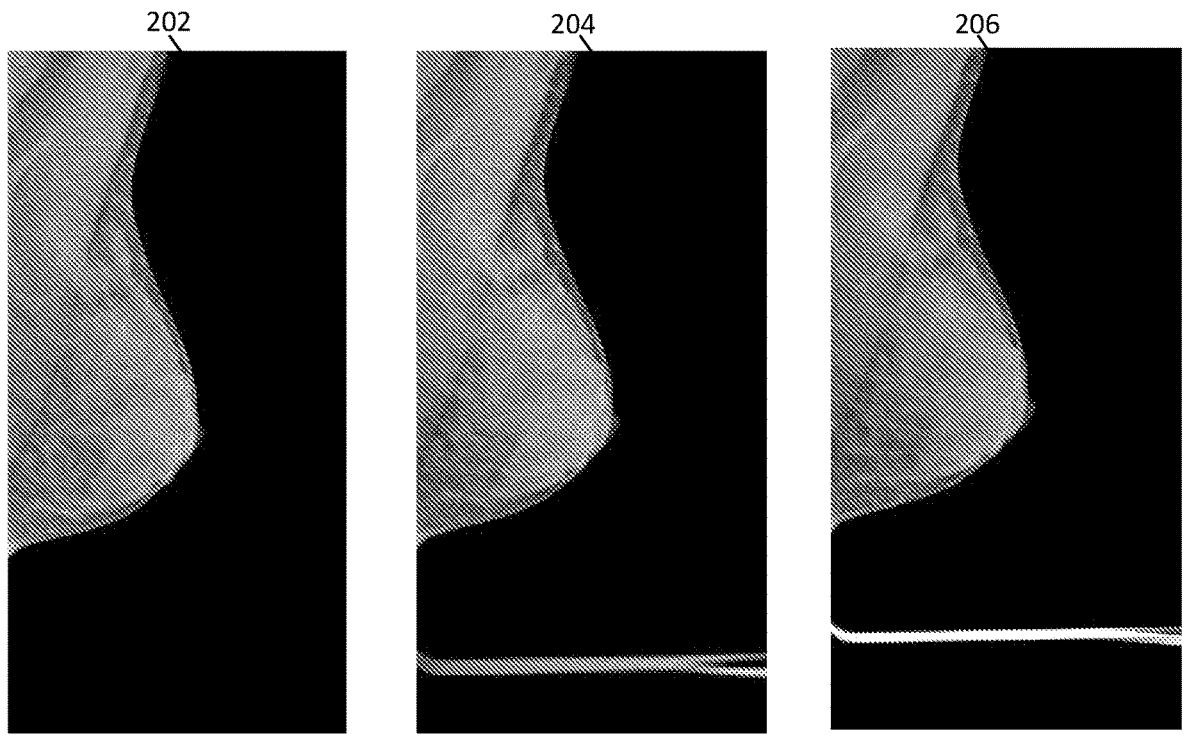
FIG. 2A depicts a plurality of projection frames for a set of tomosynthesis projection frames acquired during an MLO tomosynthesis imaging procedure.

FIG. 2A depicts a plurality of projection frames for a set of tomosynthesis projection frames acquired during an MLO tomosynthesis imaging procedure. In the example images depicted, an example first projection frame 202, and example second projection frame 204, and an example third projection frame 206 are depicted. The first MLO projection frame 202 may be the first MLO projection frame acquired during the tomosynthesis imaging procedure, the second MLO projection frame 204 may be the eighth MLO projection from acquired during the imaging procedure, and the third MLO projection frame 206 may be the fifteenth MLO projection frame acquired during the tomosynthesis imaging procedure. Accordingly, in an imaging procedure where fifteen projection frames are acquired (e.g., the x-ray source emits radiation at fifteen different angular locations), the first MLO projection frame 202 represents a beginning image, the second MLO projection frame 204 represents a middle image, and the third MLO projection frame 206 represents an end image. In each projection frame, the breast tissue as well as the pectoral muscle can be seen.

In the present technology, the boundary or edge of the pectoral muscle is identified. The identification of the edge of the pectoral muscle may be performed automatically through the use of computer-aided detection (CAD). A CAD system may analyze the projection frames to identify anatomical features, such as a pectoral muscle boundary, within the projection frames. Such identification may be based on changes between pixel values within the projection frame. For example, particular patterns of pixel intensities may be indicative a pectoral muscle boundary, and that pattern of pixel intensity allows for the CAD system to identify the boundary. Once the pectoral muscle boundary is identified, a representation of the boundary is generated. The representation of the boundary may a curve that indicates of the location of the pectoral muscle, and the curve may be based on detected locations or points of the pectoral muscle.

Figure 2B:
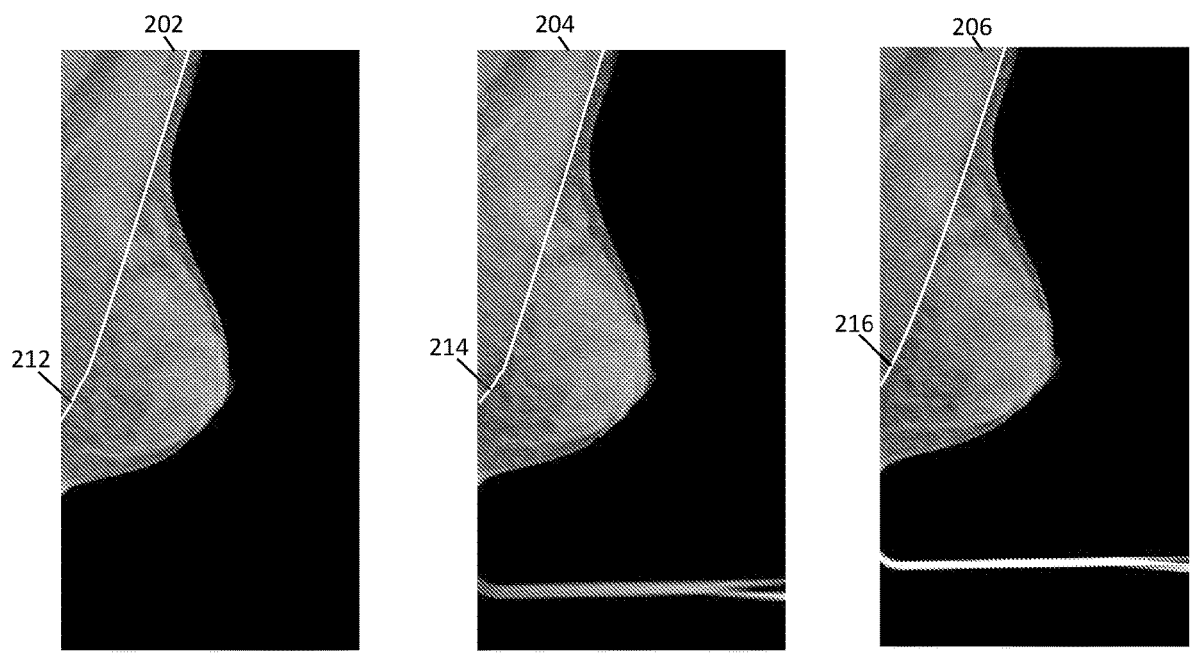
FIG. 2B depicts the plurality of projection frames of FIG. 2A with representations for the pectoral muscle boundaries.

FIG. 2B depicts the plurality of projection frames of FIG. 2A with representations for the pectoral muscle boundaries. The boundary representations are indicated by the white curve in each projection frame. The first MLO projection frame 202 includes a first boundary representation 212 for the pectoral muscle boundary identified in the first MLO projection frame 202. The second MLO projection frame 204 includes a second boundary representation 214 for the pectoral muscle boundary identified in the second MLO projection frame 206. The third MLO projection frame 206 includes a third boundary representation 216 for the pectoral muscle boundary identified in the third MLO projection frame 206. The boundary representations 212-216 follow the boundary of the pectoral muscle, which extend from the upper boundary of the respective projection frames 202-206 to approximately the middle or lower half of the chest wall. The pectoral muscle boundary passes through a substantial portion of the internal breast tissue in the projection frames. As such, motion of the pectoral muscle boundary across the acquired projection frames is a good approximation for motion of internal breast tissue.

The generated boundary representation may not be displayed in some examples. Rather, the boundary representation may be a curve defined by a function or a set of points within the image. For instance, the boundary representation may be a mathematical or plot-based representation that maybe used to perform the calculations discussed herein. The representations may be displayed in a plot, but may not be displayed as an overlay of a projection frame. The boundary representations are generally two-dimensional representations based on the two-dimensional image data in the projection frames. In some examples, however, where three-dimensional image data is available, three-dimensional boundary representations may be generated.

Figure 3A:
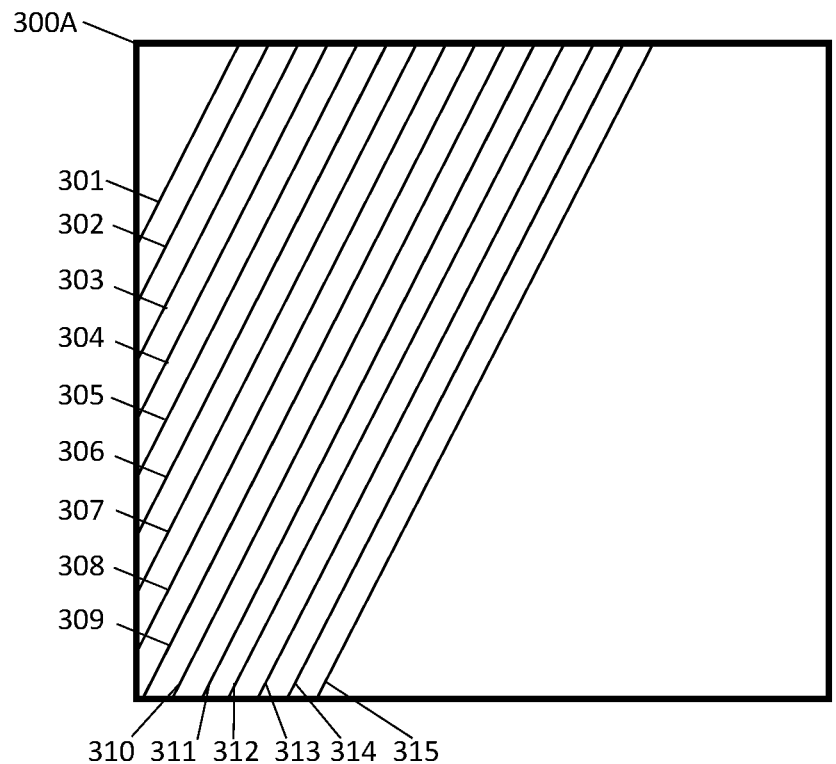
FIG. 3A depicts an example plot of pectoral muscle boundary representations where no patient motion occurred during the tomosynthesis imaging procedure.

FIG. 3A depicts an example plot 300A of pectoral muscle boundary representations 301-315 where no patient motion occurred during the tomosynthesis imaging procedure. The example plot includes pectoral muscle boundary representations 301-315 for an example MLO tomosynthesis imaging procedure where projection frames were acquired at fifteen different angular locations. Each of the pectoral muscle boundary representations 301-315 are from one of the respective projection frames acquired during that example imaging procedure.

As discussed above with respect to FIG. 1, due to the x-ray source moving around the arc, particular features of the patient appear at different locations on the receptor and thus appear in different locations in the resultant image. Accordingly, as can be seen from FIG. 3A, the boundary location and its corresponding representation occurs at a different position in each projection frame, even where there is no motion of the breast during the imaging procedure. Where there is no motion of the breast during the imaging procedure, based on the position of the first boundary muscle representation 301, the position of each other pectoral muscle boundary representation 302-315 may be predicted through mathematical or geometric calculations and/or derivations. For example, the x-ray path from the x-ray source, through the breast, and to the detector is known for each angular location of the x-ray source where x-rays are emitted. With that known path and the initial position of the first boundary muscle representation 301, the positions of the remaining boundary representations 302-315 may be predicted. While the first boundary muscle representation 301 may most often be used as a basis or starting point for predicted the remaining boundaries 302-315, any other boundary representation 301-315 may be used as a starting point for predicted the remaining boundary representations 301-315. For instance, the seventh boundary representation 307 may be used as a basis or starting point for predicting the positions of the remaining boundary representations 301-306, 308-315. The respective positions of the boundary representations 301-315 may be characterized or defined by the spacing or distance between the respective boundary representations 301-315. Even in examples where there is no motion, the spacing between each boundary representations 301-315 may not be the same. The difference in spacing between each boundary representation 301-315, however, will be smooth and predicable. Accordingly, where there is motion of the breast, the spacing between at least two boundary representations 301-315 will be different than the predicted spacing or distance between boundary representations 301-315.

Figure 3B:
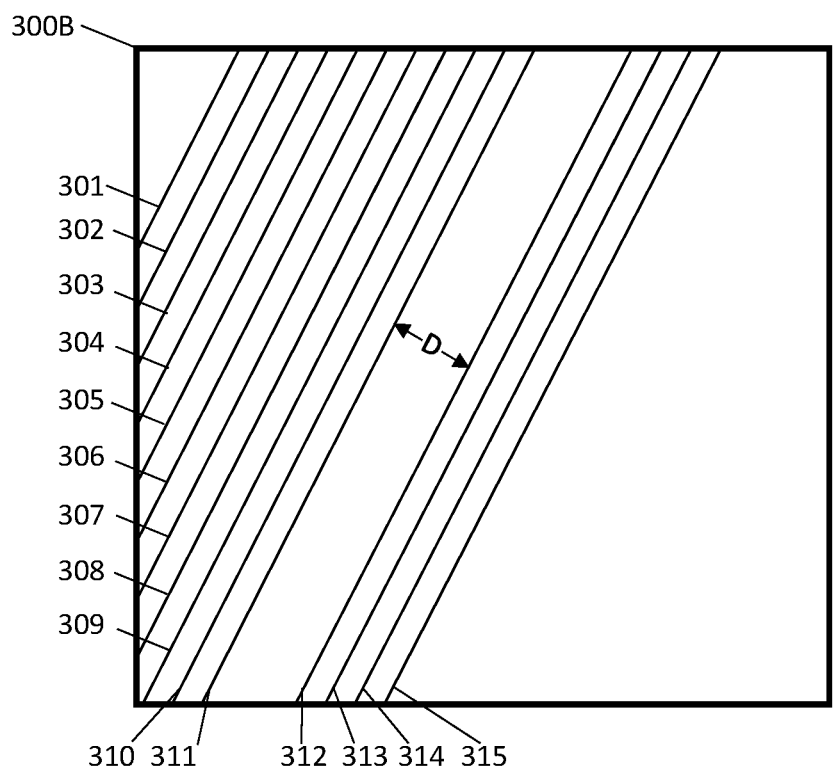
FIG. 3B depicts an example plot of pectoral muscle boundary representations where patient motion occurred during the tomosynthesis imaging procedure.

FIG. 3B depicts an example plot 300B of pectoral muscle boundary representations 301-315 where patient motion occurred during the tomosynthesis imaging procedure. In particular patient motion occurred between the time the eleventh projection frame was acquired and the time the twelfth projection frame was acquired during the tomosynthesis imaging procedure. The motion is identified based on the abnormal spacing between the eleventh boundary representation 311 and the twelfth boundary representation 312.

To determine that the spacing is abnormal and indicative of motion, a distance (D) between each pair of boundary representations 301-315 may be determined. The distance (D) may be measured in a direction that is orthogonal to at least one of the boundary representations for which the distance (D) is being calculated. For instance, a reference line that is substantially orthogonal or normal to at least one of the boundary representations 301-315 may be generated. The distance (D) may then be calculated along that reference line. The distance (D) may also be measured from a midpoint on the vertical axis for each pair of boundary representations 301-315. In some examples, the distance (D) is measured at multiple points along each of the boundary representations 301-315. The distance (D) may be measured along the boundary representation, and the minimum distance (D) may be used for further determinations and calculations. In other examples, the area between each of the boundary representations may be calculated. The area may be calculated through plot or image analysis algorithms and/or the area may be calculated by calculating the integral between the two boundary representations. The calculated distance(s) (D) and/or the calculated area between two boundary representations are may then be compared to the predicted values based on predicted positions for the ideal boundary representations without patient motion. If the calculated distance(s) (D) and/or the calculated area is different from the predicted values, it may be determined that motion has occurred. The differences between the determined distance(s) (D) and/or the calculated areas from the predicted values may be used to calculate a motion score, and if the differences are large enough, generate a motion warning.

The motion score may be based on the magnitude of the difference in position between a first boundary representation and a second generated boundary representation. For instance, a higher motion score may be generated where a determined distance (D) is large and/or the determined area between the first boundary representation and the second boundary representation is large. In addition, the motion score may be based on the difference between each pair of boundary representations for a tomosynthesis imaging procedure. For instance, in the example depicted in FIG. 3B, a difference in the form of a distance (D) and/or a determined area may be calculated or determined for the following fourteen pairs of representations: (1) boundary representation 301 and boundary representation 302; (2) boundary representation 302 and boundary representation 303; (3) boundary representation 303 and boundary representation 304; (4) boundary representation 304 and boundary representation 305; (5) boundary representation 305 and boundary representation 306; (6) boundary representation 306 and boundary representation 307; (7) boundary representation 307 and boundary representation 308; (8) boundary representation 308 and boundary representation 309; (9) boundary representation 309 and boundary representation 310; (10) boundary representation 310 and boundary representation 311; (11) boundary representation 311 and boundary representation 312; (12) boundary representation 312 and boundary representation 313; (13) boundary representation 313 and boundary representation 314; and (14) boundary representation 314 and boundary representation 315. The motion score may then be based on an aggregate of the absolute value of the determined differences between the fourteen pairs of boundary representations. The motion score may also be based on an average of the determined differences. Further, the motion score may also be based on the single greatest difference. For example, the largest determined difference for a pair of boundary representations may be used as or for the motion score. In some examples, fewer than all pairs of boundary representations may be analyzed and/or used in generating the motion score.

Figure 3C:
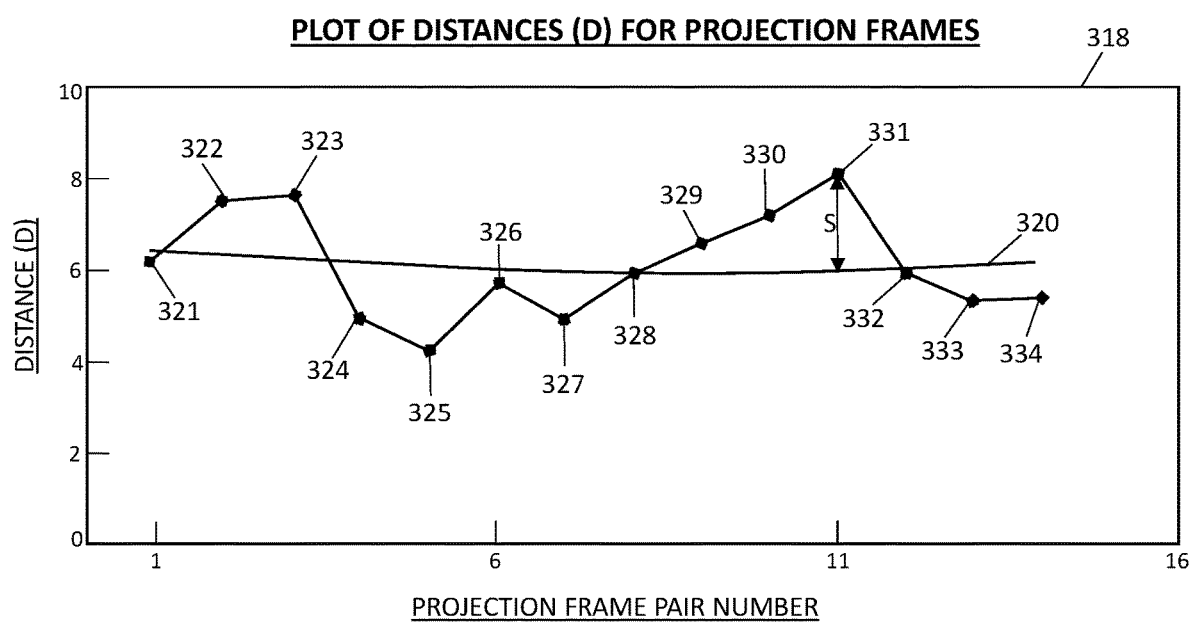
FIG. 3C depicts a plot of distances between identified of pectoral muscle boundary representations in projection frames.

FIG. 3C depicts a plot 318 of distances between identified of pectoral muscle boundary representations in projection frames. As discussed above, a distance (D) may be calculated for each pair of boundary representations. The y-axis of the plot 318 represents distance (D) and the x-axis represents the projection frame pair number. The units of the y-axis may be pixels, but other units may utilized and/or the axis may be normalized or unitless. The plot 318 displays those calculated distances (D) for 14 pairs of boundary representations, such as the fourteen pairs described above. For instance, in plot 318, there are data points displayed for a first distance 321, a second distance 322, a third distance 323, a fourth distance 324, a fifth distance 325, a sixth difference 326, a seventh distance 327, an eighth distance 328, a ninth distance 329, a tenth distance 330, an eleventh distance 331, a twelfth distance 332, a thirteenth distance 333, and a fourteenth distance 334. A curve 320 may be fitted to the plotted data points representing the distances (D). The curve 320 may be a polynomial curve, such as a second-order polynomial curve. The curve 320 may be generated through other interpolation and/or regression methods as well. The curve 320 may also be generated as a line that represents the average (median or mean) of the all the measured distances (D). The curve 320 may also represent the expected distance value for each of the projection frames. Accordingly, the expected distance may be determined from a series of projection frames. Determining the expected distance based on the fitted curve allows for the determination of the expected distance even where the geometry of the imaging system is not known or used in such a calculation. In some examples, the fitted curve 320 and the geometry of the system may both be used to determine the expected distance.

The distance or difference between a data point representing a distance (D) for a projection frame and the fitted curve 320 is referred to as the shift variance and is represented by the "S" in plot 318. The shift variance (S) represents the measured distance (D) for a respective data point and the expected value for the distance (D). As an example, the shift variance (S) represented in the plot 318 is the distance between the data point for eleventh distance 331 and the curve 320. The shift variance (S) between the respective data points and the curve 320 may be calculated based on the distance (D) measured for the projection frame pair number and the distance (D) of the curve 320 at the projection frame pair number. For example, the shift variance (S) for projection pair number eleven represented at data point 331 is approximately 2 pixels, and is based on the measured distance (D) of eight pixels at projection pair number eleven and the expected value of six pixels based on the location of the curve 320 at projection pair number eleven (e.g., the y-coordinate of curve 320 is six pixels at the x-coordinate of eleven in plot 318). A pixel is generally equal to about 0.140 mm. In some examples, the shift variance (S) between the respective data points and the curve 320 may also be calculated based on a line normal to the curve 320 from the respective data point to the curve or other minimization algorithms. If there was no patient motion during the imaging procedure, the data points would overlap with the curve 320 and the shift variance (S) values would be zero or near zero. Thus, if the shift variance (S) for any data point is greater than a predetermined threshold, internal motion of the breast likely occurred during the imaging procedure. The visual representation of the data points and the curve 320 also provides insights regarding the amount of patient motion that may have occurred as well as the type of patient motion that may have occurred.

A motion score may be generated from one or more of the shift variance (S) values. For example, where a large shift variance (S) value is determined, a high motion score may be generated. In addition, if there are multiple large shift variance (S) values calculated (e.g., large shift variance (S) values for multiple data points), a high motion score may be calculated. In contrast, where the shift variance (S) values are small, the motion score may also be small.

Figure 3D:
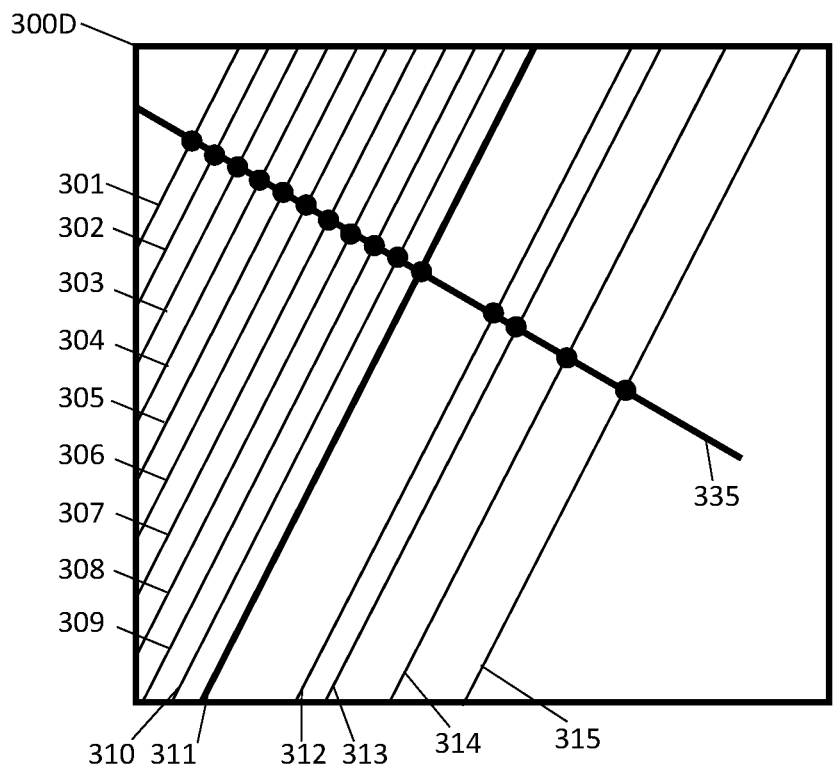
FIG. 3D a depicts another example plot of pectoral muscle boundary representations.

FIG. 3D a depicts another example plot 300D of pectoral muscle boundary representations 301-315 where patient motion occurred during the tomosynthesis imaging procedure. Similar to plots 300A-B depicted in FIGS. 3A-3B, the pectoral muscle boundary representations 301-315 are from an example MLO tomosynthesis imaging procedure where projection frames were acquired at fifteen different angular locations. Each of the pectoral muscle boundary representations 301-315 are from one of the respective projection frames acquired during that example imaging procedure.

Plot 300D also includes reference line 335. The reference line 335 is a line that is substantially normal to the boundary representations 301-315. Each of the boundary representations 301-315 intersects the reference line 335. Each intersection point is indicated by a dot in the plot. An intersection distance (I) may be determined between each of the intersection points and another reference point along the reference line. As an example, the intersection point of the eleventh boundary representation 311 from the eleventh projection frame and the reference line 335 may be used as the reference point. The boundary representation 311 has been bolded in plot 300D as a visual identifier of such an example. Any other point, even non-intersection points, along the reference line 335 may also be used as the reference point. The intersection distance (I) is the distance, along the reference line, from a respective intersection point of a boundary representation to the reference point.

Figure 3E:
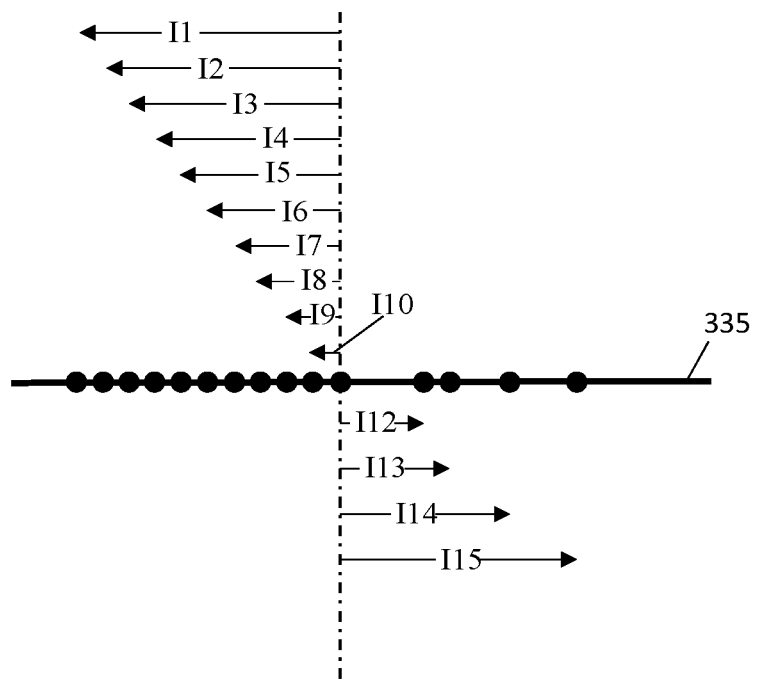
FIG. 3E depicts example intersection distance (I) measurements.

FIG. 3E depicts example intersection distance (I) measurements or calculations. Continuing with the example in plot 300D in FIG. 3D, the intersection point between boundary representation 311 and the reference line 335 has been selected as the reference point. Accordingly, an intersection distance (I) is determined for each boundary representation from the selected reference point. Because there are fifteen projection frames taken in the example imaging procedure, fifteen intersection distances (I) may be calculated or measured. For example, the following intersection distances (I) may be calculated or measured: (1) an intersection distance (I1) between the first boundary representation 301 and the reference point; (2) an intersection distance (I2) between the second boundary representation 302 and the reference point; (3) an intersection distance (I3) between the third boundary representation 303 and the reference point; (4) an intersection distance (I4) between the fourth boundary representation 304 and the reference point; (5) an intersection distance (I5) between the fifth boundary representation 305 and the reference point; (6) an intersection distance (I6) between the sixth boundary representation 306 and the reference point; (7) an intersection distance (I7) between the seventh boundary representation 307 and the reference point; (8) an intersection distance (I8) between the eighth boundary representation 308 and the reference point; (9) an intersection distance (I9) between the ninth boundary representation 309 and the reference point; (10) an intersection distance (I10) between the tenth boundary representation 310 and the reference point; (11) an intersection distance (I11) between the eleventh boundary representation 311 and the reference point; (12) an intersection distance (I12) between the twelfth boundary representation 312 and the reference point; (13) an intersection distance (I13) between the thirteenth boundary representation 313 and the reference point; (14) an intersection distance (I14) between the fourteenth boundary representation 314 and the reference point; and (15) an intersection distance (I15) between the fifteenth boundary representation 315 and the reference point. Of note, intersection distance I11 is not depicted in FIG. 3E because the reference point in the present example has been selected to be the intersection point of the eleventh boundary representation and the reference line 335. Thus, in the present example, the intersection distance I11 is zero. The intersection distances (I) may be used to determine whether patient motion occurred during the imaging procedure as discussed below. In examples where fewer projection frames are captured during an imaging procedure, fewer intersection distances (I) are calculated or measured. Similarly, in examples where more projection frames are captured during an imaging procedure, more intersection distances (I) may be calculated or measured.

Figure 3F:
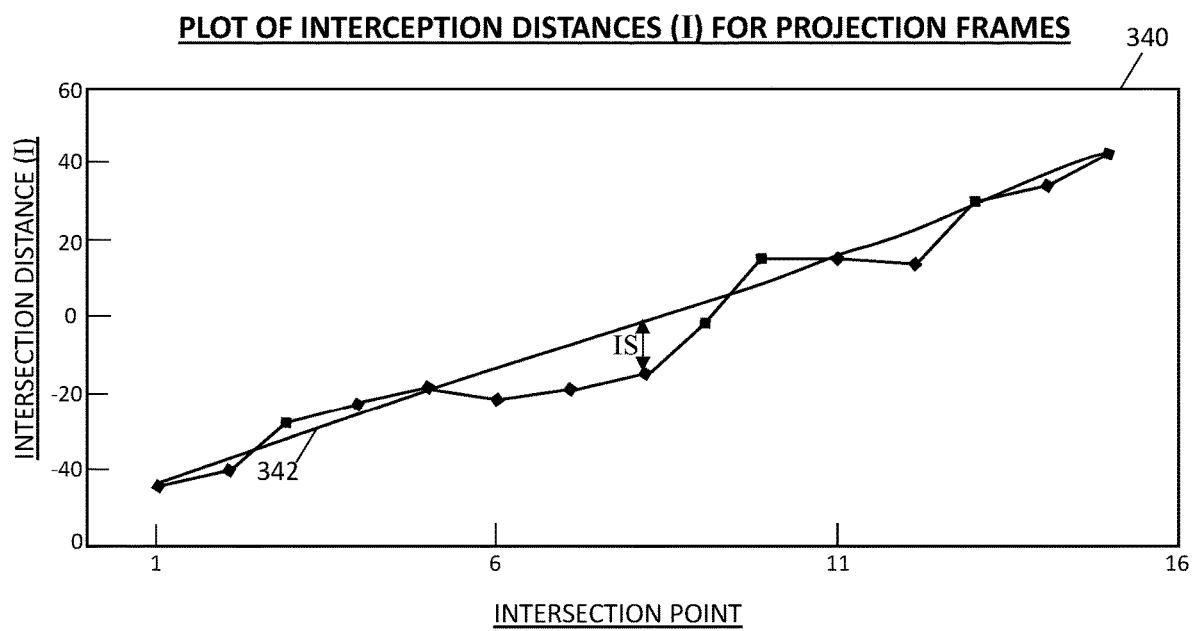
FIG. 3F depicts an example plot of intersection distances (I).

FIG. 3F depicts an example plot 340 of intersection distances (I) for intersection points of boundary representations 301-315 with the reference line 335. In the example plot 340, fifteen data points are plotted representing intersection distances (I) for fifteen intersection points. The y-axis of the plot 340 represents the interception distance (I) value and the x-axis of the plot represents the projection frame or boundary representation number. The units of the y-axis may be pixels, but other units may utilized and/or the axis may be normalized or unitless. Because of breast motion during the imaging procedure, the intersection distances are not uniform and the data points in the plot do not follow a straight line. A curve 342 may be fitted to the data points. The curve 342 may a polynomial curve, such as a second-order polynomial. The curve 342 may be generated through other interpolation and/or regression methods as well. The curve 342 may represent the expected intersection distance (I) for each intersection point.

The distance or difference between a data point representing an intersection distance (I) for a projection frame and the fitted curve 342 is referred to as the intersection shift variance and is represented by the "IS" in plot 340. The intersection shift variance (IS) may be calculated similarly to the shift variance (S) discussed above. For instance, the intersection shift variance (IS) between the respective data points and the curve 342 may be calculated based the intersection distance (I) measured for the intersection point and the distance (I) of the curve 342 at the intersection point. If there was no patient motion during the imaging procedure, the data points would overlap with the curve 342 and the intersection shift variance (IS) values would be zero or near zero. Thus, if the intersection shift variance (IS) for any data point is greater than a predetermined threshold, internal motion of the breast likely occurred during the imaging procedure. The visual representation of the data points and the curve 342 also provides insights regarding the amount of patient motion that may have occurred as well as the type of patient motion that may have occurred.

A motion score may be generated from one or more of the intersection shift variance (IS) values. For example, where a large intersection shift variance (IS) value is determined, a high motion score may be generated. In addition, if there are multiple large intersection shift variance (IS) values calculated (e.g., large intersection shift variance (IS) values for multiple data points), a high motion score may be calculated. In contrast, where the intersection shift variance (IS) values are small, the motion score may also be small.

Figure 4A:
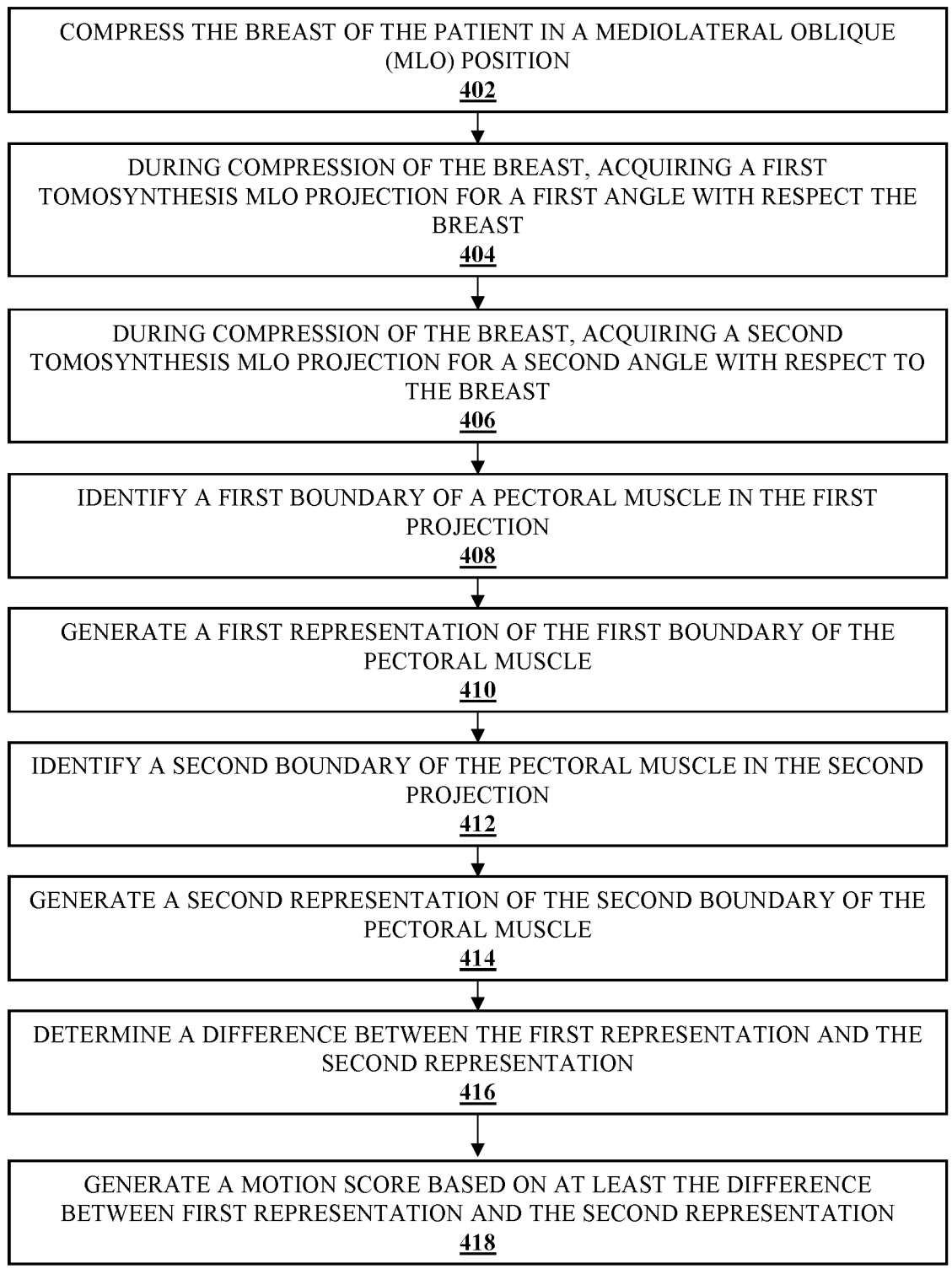
FIG. 4A depicts an example method for approximating or identifying motion of internal breast tissue during a tomosynthesis procedure.

FIG. 4A depicts an example method 400 for approximating or identifying motion of internal breast tissue during a tomosynthesis procedure. At operation 402, a breast of a patient is compressed in the MLO position. As discussed above, this position is often about 45 degrees from vertical, but may be between approximately 30-60 degrees in some examples and depending on the needs of the particular patient. In some examples, compressing the breast includes placing the breast on the breast platform and moving the compression paddle towards the breast platform until the breast is compressed therebetween. During compression of the breast, a first tomosynthesis MLO projection frame is acquired at operation 404. The first tomosynthesis MLO projection frame may be for a first angle with respect to the breast. For example, the first tomosynthesis MLO projection frame may be acquired by emitted x-ray radiation from the x-ray source at a first angle along the arc, as depicted in FIG. 1. At operation 406, during compression of the breast, a second tomosynthesis MLO projection frame is acquired. The second tomosynthesis MLO projection frame may be for a second angle with respect to the breast. For example, the second tomosynthesis MLO projection frame may be acquired by emitted x-ray radiation from the x-ray source at a second angle along the arc, as depicted in FIG. 1. Operation 404 and 406 may be performed during the same compression of the breast. That is, the breast is compressed for a continuous period while the projection frames are acquired. While not depicted in method 400, the method 400 may include acquiring additional tomosynthesis MLO projection frames for additional angles as well.

After the MLO projection frames are acquired, boundaries for the pectoral muscle are identified. At operation 408, a first boundary of a pectoral muscle in the first MLO projection frame is identified. The first boundary of the pectoral muscle in the first projection frame may be identified through the use of CAD techniques, as discussed above. At operation 410, a first representation for the identified first boundary of the pectoral muscle is generated. The generated first boundary representation may be one of the boundary representations depicted above in FIG. 2B and/or FIGS. 3A-3B, 3D. At operation 412, a second boundary of the pectoral muscle in the second MLO projection frame is identified. The second boundary of the pectoral muscle in the projection frame may be identified through the use of CAD techniques, as discussed above. At operation 414, a second representation for the identified second boundary of the pectoral muscle is generated. The generated second boundary representation may be one of the boundary representations depicted above in FIG. 2B and/or FIGS. 3A-3B, 3D. As an example, the first generated boundary representation may be boundary representation 301 in FIGS. 3A-3B and/or 3D and the generated second boundary representation may be boundary representation 302 in FIGS. 3A-3B and/or 3D. Any other combination of the boundary representations 301-315 from FIGS. 3A-B and/or 3D may also be the generated first boundary representation and the second boundary representation.

At operation 416, a difference between the first boundary representation and the second boundary representation is determined. The difference may be a difference in position between the first boundary representation and the second boundary representation in the respective projection frames. For example, the difference may be the distance (D) discussed above and depicted in FIG. 3B. The difference may also be the area between the two generated boundary representations, as discussed above. The difference may also be a minimum distance between the first boundary representation and the second boundary representation.

At operation 418, a motion score is generated based on at least the difference between the first generated boundary representation and the second generated boundary representation. The motion score may be based on the magnitude of the difference in position between the first generated boundary representation and the second generated boundary representation. For instance, a higher motion score may be generated where a determined distance (D) is large and/or the determined area between the first generated boundary representation and the second generated boundary representation is large. In addition, the motion score may be based on the difference between each pair of generated boundary representations for a tomosynthesis imaging procedure. The motion score may be based on an aggregate of the absolute value of the determined differences between the possible pairs of boundary representations. The motion score may also be based on an average of the determined differences. Further, the motion score may also be based on the single greatest difference. For example, the largest determined difference for a pair of boundary representations may be used as, or for, the motion score. The motion score may be used automatically to adjust or dispose of projection frames most affected by patient motion. For example, if a subset of the projection frames exhibit motion, image reconstruction might be performed without that subset of projection frames that have been affected by motion, or performed with all projection frames after correction has been applied to the affected subset of projection frames. Such motion-score-based processing may include proper global and local adjustment, transformation, and shift back to correct the motion amount. In addition, motion scores may be used to prompt and perform filtering to suppress the high-frequency content to prevent contamination (blurring) of any final images while passing the low frequency content to improve the signal to noise ratio of final images. The motion score may also be compared to a predetermined threshold, and if the motion score is greater than a predetermined threshold, a motion warning may be generated.

Figure 4B:
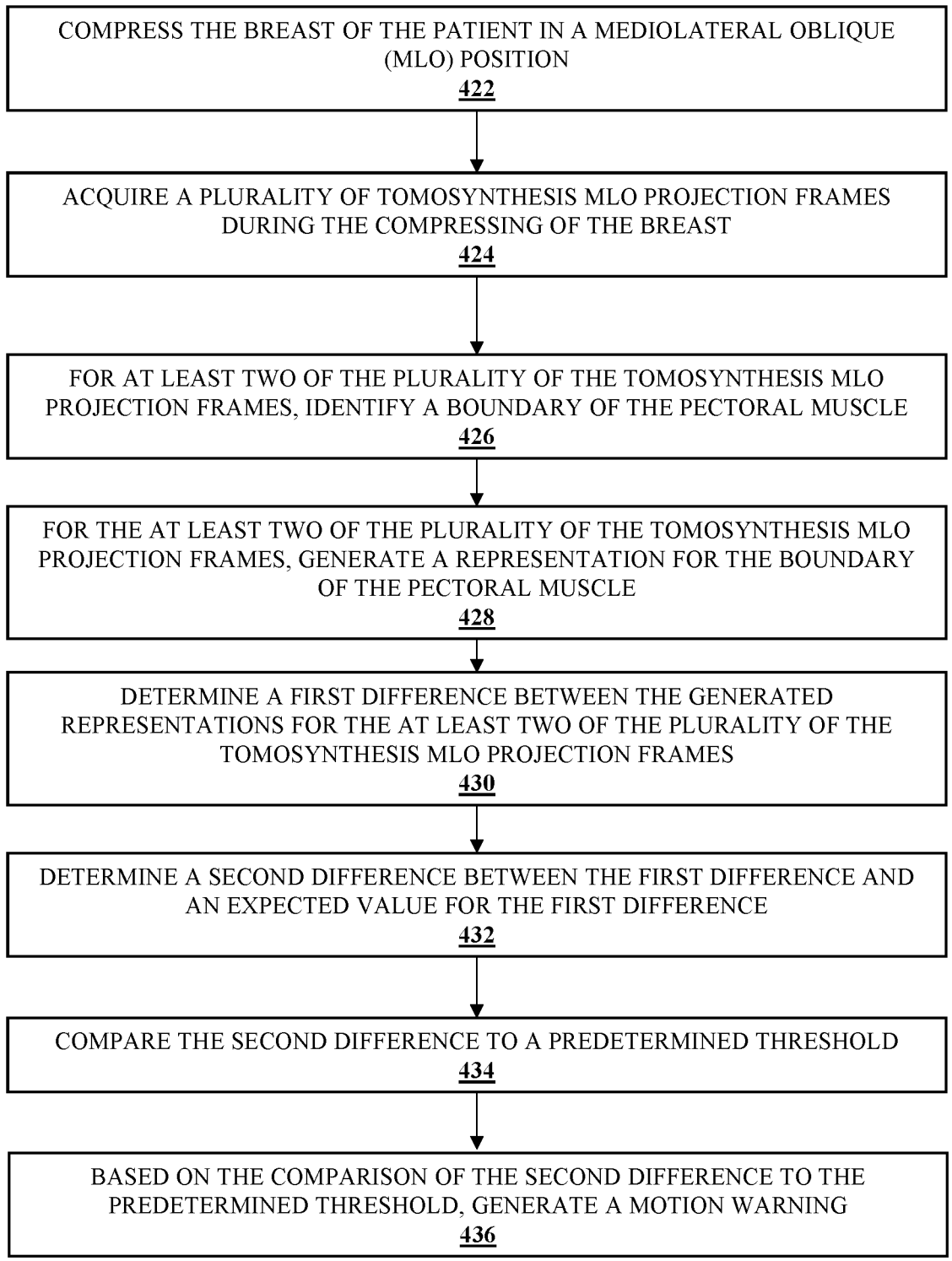
FIG. 4B depicts another example method for approximating or identifying motion of internal breast tissue during a tomosynthesis procedure.

FIG. 4B depicts another example method 420 for approximating or identifying motion of internal breast tissue during a tomosynthesis procedure. At operation 422, a patient's breast is compressed in an MLO position. The compression may be the same as operation 402 in method 400 depicted in FIG. 4A. At operation 424, a plurality of tomosynthesis MLO projection frames are acquired during the compression of the breast. For example, while the patient's breast in compressed, a series of projection frames are acquired during the tomosynthesis imaging procedure as the x-ray source moves around the arc as depicted in FIG. 1.

At operation 426, a boundary for the pectoral muscle is identified in at least two of the projection frames acquired in operation 424. The boundaries of the pectoral muscle in the projection frames may be identified through the use of CAD techniques, as discussed above. At operation 428, a representation for the boundary of the identified pectoral muscle is generated for each of the at least two projection frames for which the boundary of the pectoral muscle was identified. The boundary representations generated in operation 428 may be any of the boundary representations discussed above.

At operation 430, a first difference between the generated boundary representations is determined. For instance, the first difference may be any of the differences in position between two boundary representations discussed above, such as a distance (D) between the two boundary representations and/or an area between the two boundary representations. At operation 432, a difference between the first difference and the expected value for the first difference is determined. The expected value may be based on curve fitted to a plurality of differences calculated for projection frame pairs, such as curve 320 depicted in FIG. 3C. In such an example, the difference between the first difference and the expected value is the shift variance (S) for the first projection frame pair. In addition, as discussed above, the position of the various boundary representations is predictable where there is no motion of the breast during the imaging procedure. Thus, the difference between two boundary representations is also predicable and determinable. Based on the predicted position of the boundary representations, an expected value for the difference between any two boundary representations may be determined based on the geometry of the imaging system. Accordingly, in some examples, the expected value may be calculated based, in part, on the x-ray angle of the source for each respective projection frame.

If the first difference determined in operation 430 is different from the expected value for the first difference, motion is likely to have occurred during the time that the two corresponding projection frames were acquired. The magnitude of the difference determined in operation 432 (e.g., the shift variance (S)) is generally indicative of the amount of motion that occurred between the two projection frames for which the boundary representations were generated and used for calculations and determinations.

At operation 434, the difference determined in operation 432 (e.g., the shift variance (S)) is compared to a predetermined threshold. The predetermined threshold may be a threshold for which an amount of motion is acceptable. For instance, a small amount of motion during the imaging procedure may be acceptable in some situations. Accordingly, the predetermined threshold may be set at a magnitude of motion that does not result in a degradation in image quality and/or would still result in clinically acceptable reconstructions and tomosynthesis slices. At operation 436, a motion warning may be generated based on the comparison performed at operation 434. For example, if the difference determined at operation 432 between the expected value and the first value is greater than the predetermined threshold, a motion warning may be generated. The motion warning may indicate to a reviewer that internal breast tissue motion occurred during the tomosynthesis imaging procedure. The warning may further indicate between which projection frames the motion occurred and the severity of the motion. The motion warning may also be an audible warning, such as an emitted sound, to alert that motion occurred during the imaging procedure. When the motion warning is provided, the technician may then immediately re-image the patient, which prevents the patient from having to return to the imaging facility at a later date.

Figure 4C:
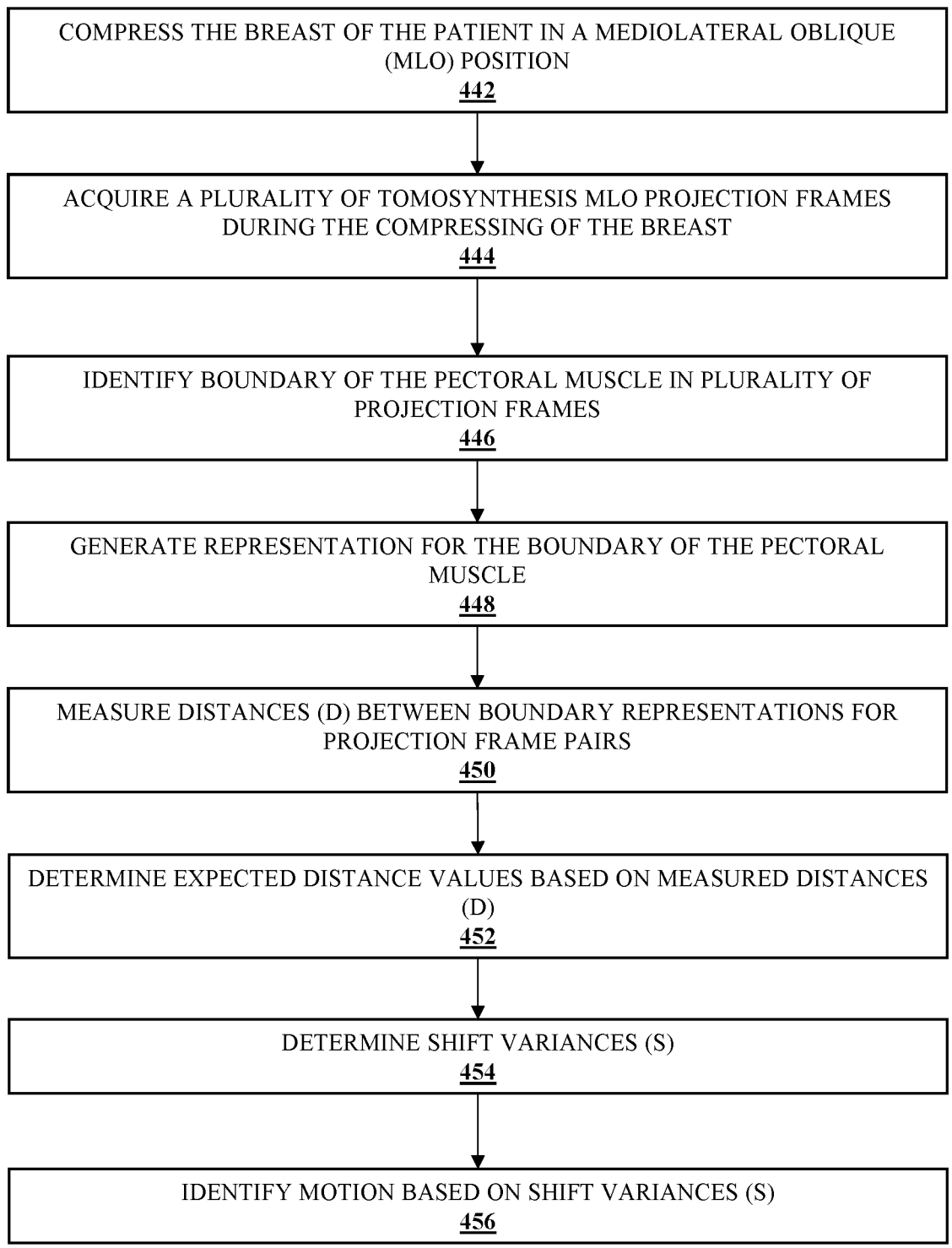
FIG. 4C depicts another example method for approximating or identifying motion of internal breast tissue during a tomosynthesis procedure.

FIG. 4C depicts another example method 440 for approximating or identifying motion of internal breast tissue during a tomosynthesis procedure. At operation 442, a patient's breast is compressed and, at operation 444, a plurality of tomosynthesis projection frames are acquired during compression of the breast. For example, fifteen projection frames may be acquired. In some examples, at least three projection frames are acquired. Operations 442 and 444 may the same as operations 422 and 424 of method 420 depicted FIG. 4B. At operation 446, a boundary of the pectoral muscle is identified in the plurality of projection frames acquired in operation 444. In some examples, a boundary of the pectoral muscle may be identified for each of the projection frames in the plurality of projections frames or for a subset thereof. The boundaries of the pectoral muscle in the projection frames may be identified through the use of CAD techniques, as discussed above. At operation 448, a representation is generated for each of boundaries identified in operation 448. The boundary representations generated in operation 448 may be any of the boundary representations discussed above. In some examples, boundary representations may be generated for less than all of the projection frames acquired in operation 444. For instance, boundary representations may be generated for at least a subset of the boundaries identified in operation 446.

At operation 450, distances (D) are measured or calculated between each pair of boundary representations generated in operation 448. The distance (D) may be the distance (D) discussed above and/or depicted in FIG. 3B. In some examples, distances (D) may be measured for less than all the possible pairs of boundary representations. For instance, distances (D) may be measured or calculated for at least a subset of all possible pairs of boundary representations.

At operation 452, expected distance values are determined based on the measured distances (D) of operation 450. Determining the expected distance values may include fitting a curve to the measured distances, such as curve 320 discussed above and depicted in FIG. 3C. In some examples, the measured distances (D) may be co-plotted and the fitted curve may be a polynomial curve, such as a second-order polynomial curve. The fitted curve may also be generated using any of the other techniques discussed above. The fitted curve may then be used to generate an expected distance value for each of the boundary representation pairs and/or projection frame pairs.

At operation 454, shift variance (S) values are determined for each of the boundary representation pairs for which a distance (D) is measured or calculated in operation 452. The shift variance (S) value is the difference between the measured distance (D) for a boundary representation pair and the expected distance value for the boundary pair representation. In some examples, the a shift variance (S) value for less than all the possible pairs of boundary representations the boundary representation pairs for which a distance (D) is measured or calculated. For instance, shift variances (S) may be calculated for at least a subset of the boundary representation pairs for which a distance (D) is measured or calculated. The shift variance (S) value is the difference between the measured distance (D) for a boundary representation pair and the expected distance value for the boundary pair representation.

At operation 456, patient motion during the imaging procedure is identified based on the shift variances (S) determined in operation 454. The identification of motion may be based on comparing the shift variances (S) to a predetermined threshold. If any shift variance (S) is greater than the predetermined threshold, patient motion may be determined to have occurred. An average of the shift variance (S) values may also be compared to a predetermined threshold to determine whether patient motion occurred. If patient motion is identified in operation 456, a motion warning may be generated. The motion warning may indicate to a reviewer that internal breast tissue motion occurred during the tomosynthesis imaging procedure. The warning may further indicate between which projection frames the motion occurred based on which boundary representation pair produced the large shift variance (S) value. The motion warning may also include an indication of the severity of the motion based on the magnitude of the shift variance (S) values and/or the magnitude of the different between shift variance (S) value and the predetermined threshold. The motion warning may also be an audible warning, such as an emitted sound, to alert that motion occurred during the imaging procedure. A motion score may also be generated from one or more of the shift variance (S) values. For example, where a large shift variance (S) value is determined, a high motion score may be generated. In addition, if there are multiple large shift variance (S) values calculated (e.g., large shift variance (S) values for multiple data points), a high motion score may be calculated. In contrast, where the shift variance (S) values are small, the motion score may also be small.

Figure 4D:
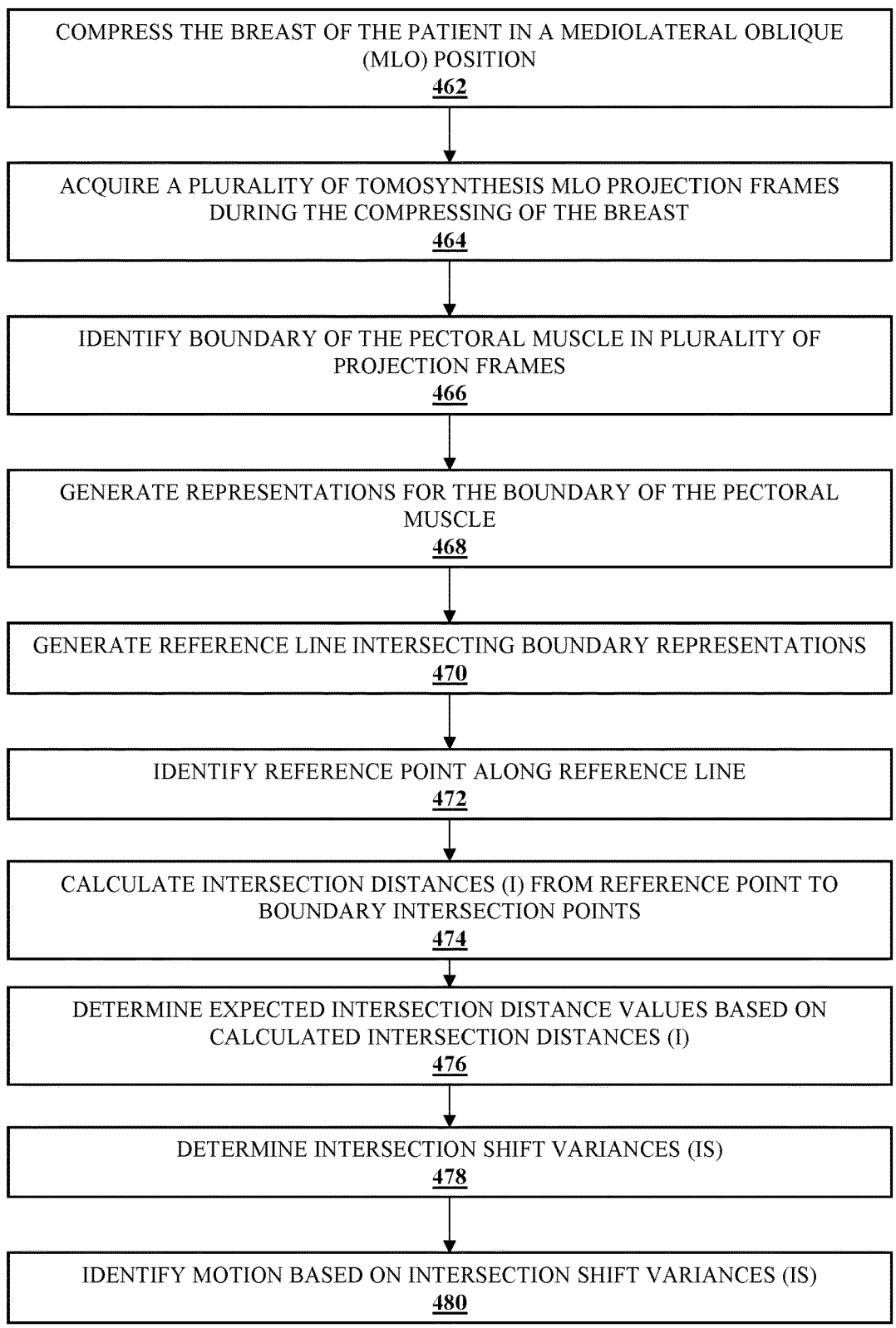
FIG. 4D depicts another example method for approximating or identifying motion of internal breast tissue during a tomosynthesis procedure.

FIG. 4D depicts another example method 460 for approximating or identifying motion of internal breast tissue during a tomosynthesis procedure. At operation 462, a patient's breast is compressed and, at operation 464, a plurality of tomosynthesis projection frames are acquired during compression of the breast. For example, fifteen projection frames may be acquired. In some examples, at least three projection frames are acquired. Operations 462 and 464 may the same as operations 442 and 444 of method 440 depicted FIG. 4C. At operation 466, a boundary of the pectoral muscle is identified in the plurality of projection frames acquired in operation 464, and at operation 468 representations are generated for those boundaries. Operations 462-468 may the same as operations 442-448 of method 440 depicted FIG. 4C.

At operation 470, a reference line or curve intersecting the boundary representations is generated. The reference line may be reference line 335 depicted in FIG. 3D. Operation 470 may include co-plotting the boundary representations generated in operation 468. In some examples, less than all of the generated boundary representations may be used. For instance, at least a subset of the boundary representations generated in operation 468 may be plotted and used for the other calculations or measurements in method 460. With the boundary representations co-plotted, the reference line may be generated such that the reference line intersects each of the co-plotted boundary representations. In some examples, the reference line may be normal to, or approximately normal to, one or more of the boundary representations. At operation 472, a reference point along the reference line is identified or selected. The reference point may be any point along the reference line. In some examples, the reference point may be selected as one of points where the reference line intersects a boundary representation.

At operation 474, intersection distances (I) are calculated or measured. The intersection distance (I) is the distance between the reference point and an intersection point of a boundary representation and the reference line, as discussed above with reference to FIGS. 3D-3E. Accordingly, operation 474 may also include identifying intersection points for the boundary representations and the reference line. An intersection distance (I) may be measured or calculated for each boundary representation or at least a subset of the boundary representations.

At operation 476, expected intersection distance (I) values are determined. The expected intersection distances may be determined based on the measured intersection distances (I) that are measured in operation 474. For example, the measured intersection distances (I) may be co-plotted as data points and a curve may be fitted to the data points, as discussed above with reference to FIG. 3F. For instance, the curve 342 depicted in FIG. 3F may be generated based on the intersection distances calculated in operation 474. The curve may then be used to generate or calculate the expected intersection distance values.

At operation 478, intersection shift variances (IS) may be calculated for each of the boundary representations or at least a subset of the boundary representations. The intersection shift variance (IS) is the difference between the measured intersection distance (I) for a boundary representation (measured in operation 474) and the expected value for the intersection distance (determined in operation 476). The intersection shift variance (IS) may be determined or calculated using any of the methods or processes discussed above. For instance, the intersection shift variance (IS) may be calculated as a difference or distance between the respective data points representing the measured intersection distances (I) and a curve fitted to those data points, such as curve 342 depicted in FIG. 3F.

At operation 480, patient motion during the imaging procedure is identified based on the intersection shift variance (IS) values determined in operation 478. The identification of motion may be based on comparing the intersection shift variance (IS) values to a predetermined threshold. If any intersection shift variance (IS) value is greater than the predetermined threshold, patient motion may be determined to have occurred. An average of the intersection shift variance (IS) values may also be compared to a predetermined threshold to determine whether patient motion occurred. If patient motion is identified in operation 480, a motion warning may be generated. The motion warning may indicate to a reviewer that internal breast tissue motion occurred during the tomosynthesis imaging procedure. The warning may further indicate between which projection frames the motion occurred based on which boundary representation pair produced the large intersection shift variance (IS) value. The motion warning may also include an indication of the severity of the motion based on the magnitude of the intersection shift variance (IS) values and/or the magnitude of the different between an intersection shift variance (IS) value and the predetermined threshold. The motion warning may also be an audible warning, such as an emitted sound, to alert that motion occurred during the imaging procedure. A motion score may also be generated from one or more of the intersection shift variance (IS) values. For example, where a large intersection shift variance (IS) values value is determined, a high motion score may be generated. In addition, if there are multiple large intersection shift variance (IS) values calculated (e.g., large intersection shift variance (IS) values for multiple data points), a high motion score may be calculated. In contrast, where the intersection shift variance (IS) values are small, the motion score may also be small.

Figure 5A:
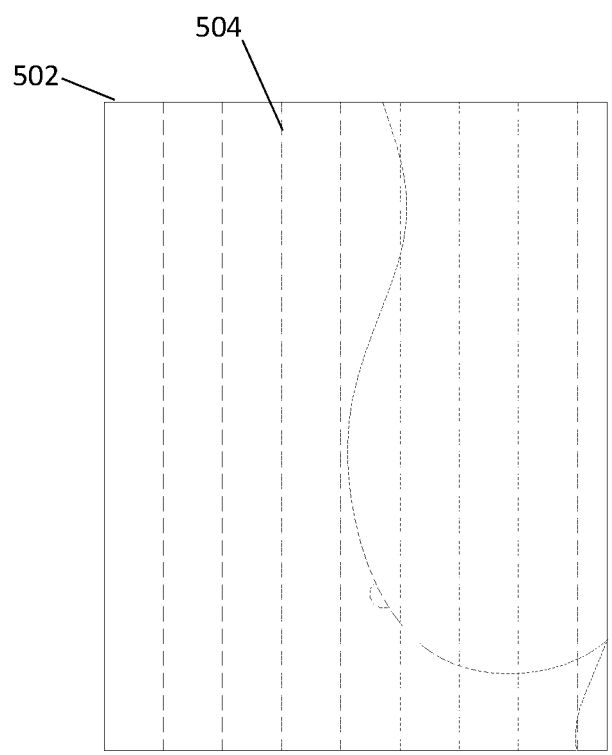
FIG. 5A depicts an example medical image of a breast with a plurality of motion guides.

FIG. 5A depicts an example medical image 502 of a breast with a plurality of motion guides 504. The medical image 502 may be a tomosynthesis projection frame acquired during a tomosynthesis imaging procedure. In the example depicted, the motion guides 504 are a plurality of parallel vertical lines that are evenly spaced from one another. The motion guides 504 provide a reference frame for the location of features of breast. When two images are thus compared to one another, one can more easily discern whether a feature of the breast has moved between the time the first image was captured and the time the second image was captured. The images may be compared to one another by having the images displayed concurrently or consecutively, such as in a cine mode. In some examples, each individual motion guide 504 is selectable and configurable. For instance, a motion guide 504 may be selected and dragged to a new location within the image. Such a feature is a desirable where a reviewing physician may want a motion guide 504 to be directly aligned with a feature or region of interest of the breast, such as the nipple or a lesion. The configurability of the motion guides 504 is also desirable when the reviewing physician wishes to move a particular motion guide 504 out of view such that the motion guide 504 does not obscure the image of the breast itself. In some examples, each motion guide may be deleted and/or new motion guides may be added. The display of the motion guides may also be toggled on and off by a reviewing physician through a user interface features that is displayed concurrently with the medical image 502. While the motion guides 504 are depicted as being vertical, parallel, evenly spaced, and having fixed locations in the example depicted, the motion guides 504 may be non-parallel, non-vertical, and/or unevenly spaced in other examples. The motion guides 504 may also have varying locations. For example, the motion guides 504 may also include horizontal lines to provide a reference frame for vertical motion. The horizontal lines may progressively move down for each increasing projection frame due to compensate for movement of the tube moving along the arc (as discussed above), which cause the breast in the projection frames to appear to move downward.

Figure 5B:
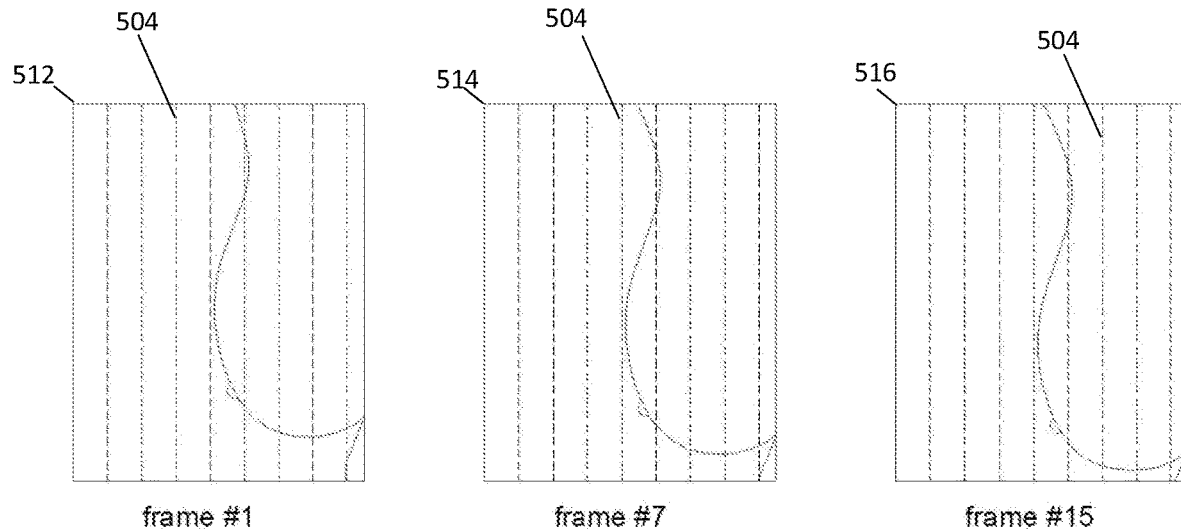
FIG. 5B depicts an example series of projection frames for a tomosynthesis imaging procedure of a stationary breast.

FIG. 5B depicts an example series of projection frames 512-516 for a tomosynthesis imaging procedure of a stationary breast. More specifically, an example first projection frame 512, an example seventh projection frame 514, and an example fifteenth projection frame 516. Motion guides 504 are displayed in each of the projections frames 512-516. As can be seen from a comparison of the projection frames 512-516, the breast appears to have moved downward during the tomosynthesis imaging procedure. However, this apparent movement is due to the movement of the x-ray tube along the arc, as discussed above with respect to FIG. 1. The breast, however, remained stationary during the example imaging procedure that produced the example projection frames 512-516. The projection frames 512-516 may be displayed concurrently or sequentially, such as in a cine mode where the projection frames 512-516 may be played as a video that includes the sequence of projection frames.

Figure 5C:
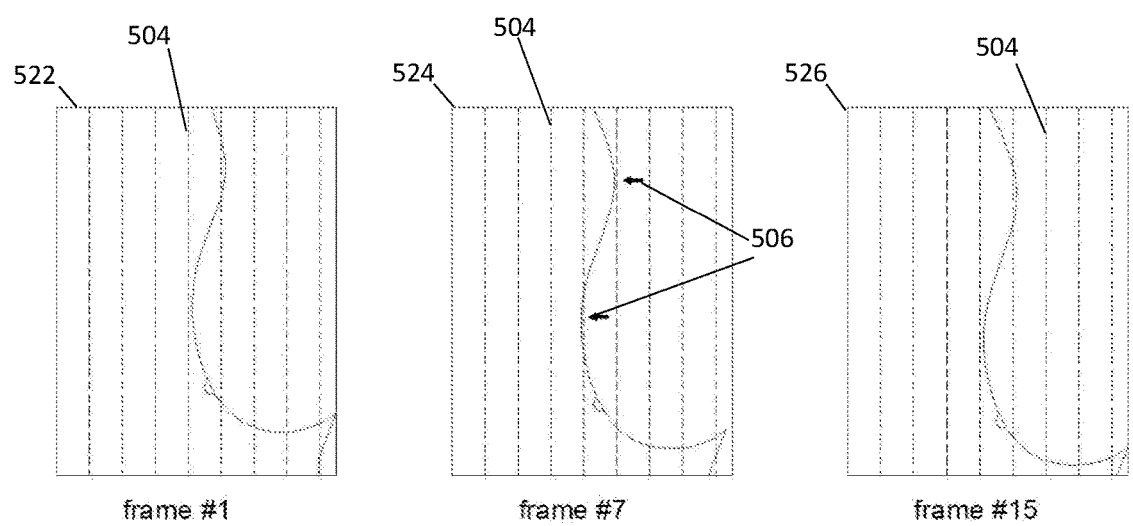
FIG. 5C depicts an example series of projection frames where breast motion occurred during a tomosynthesis imaging procedure.

FIG. 5C depicts an example series of projection frames 522-526 where breast motion occurred during a tomosynthesis imaging procedure. The series of projection frames 522-526 are substantially similar to the projection frames 512-516 depicted in FIG. 5B with the exception that the breast in projection frames 522-526 in FIG. 5B was in motion between the time the first projection frame 522 was acquired and the time the seventh projection frame 524 was acquired. The motion of the breast, which is horizontal motion in the example depicted, can be seen more easily due to the motion guides 504. As can be seen from the projection frames 522-526, the breast shifts across at least one of the motion guides. In addition, when motion is detected or identified, as through the methods or processes discussed herein, a motion indicator 506 may be displayed on one or more of the projection frames 522-526. The motion indicator 506 may indicate the direction of the motion as well as the magnitude of the motion. For instance, in examples where the motion indicator 506 is an arrow, the arrow points in the direction of the motion, and the size or color of the arrow may indicate the magnitude of the motion. The magnitude of the motion may be based on the motion score. The motion indicator 506 may also be based on motion of the breast as compared to the previous projection frame. In some examples, the motion indicator 506 may be displayed temporarily and may be toggled on and off. The motion indicator 506 may also be displayed in an area of the projection frame that does not overlap with the breast so as to not obstruct the view of the breast. While depicted as an arrow, the motion indicator 506 may be other visual indicators. For example, the motion indicator may be a representation of the motion score for the imaging procedure, which may be represented in numerically, alphabetically, in different colors, or other visual indications to indicate the magnitude of the motion score. The projection frames 522-526 may be displayed concurrently or sequentially, such as in a cine mode where the projection frames 522-526 may be played as a video that includes the sequence of projection frames.

Figure 6:
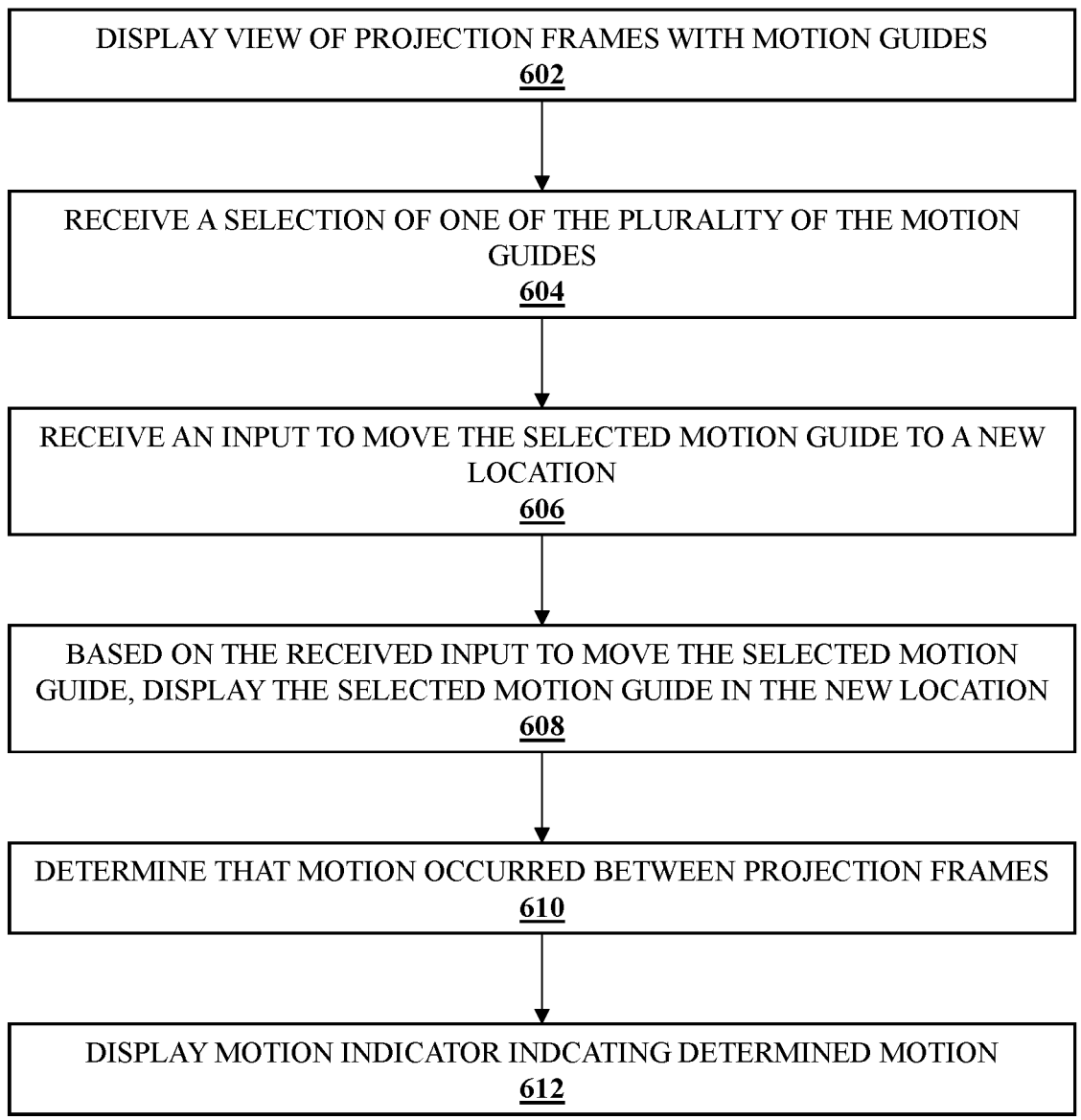
FIG. 6 depicts an example method for displaying motion guides for a medical image.

FIG. 6 depicts an example method 600 for displaying motion guides for a medical image. At operation 602, a view of projection frames with a plurality of motion guides is displayed on a display, such as a display at a workstation or remote viewing station. The view of the projections may include concurrently displaying the projection frames or displaying the projection frames sequentially, such as in a cine mode. At operation 604, a selection of one of the motion guides is received. The selection may be made through any input mechanism, such as via a mouse, trackball, or touch input. At operation 606, an input is received that indicates the selected motion guide is to be moved to a new location. The input may be in the form of a dragging motion or other input means for indicating a new location for the motion guide. Based on receiving the input to move the selected motion guide, the selected motion guide is displayed at the new location in operation 608. Movement of one or more of the motion guides may be desired where the motion guide is obstructing a portion of breast or where the reviewing physician desires to align one or more of the motion guides with a particular anatomical structure of the breast or other landmark. When a motion guide has been moved, the moved motion guide may appear in each projection frame at the new location. As such, during a cine mode, the motion guides do not change position as the projection frames are displayed.

At operation 610, a determination is made that breast motion occurred between at least two of the projection frames that are displayed or are to be displayed. Determining that breast motion occurred may be performed by any of the techniques discussed herein. The determination of breast motion in operation 610 may also include a determination of a direction and/or magnitude of the motion. Based on the determined breast motion in operation 610, a motion indicator is displayed in operation 612. The motion indicator may be the example motion indicator 506 depicted in FIG. 5B.

Figure 7:
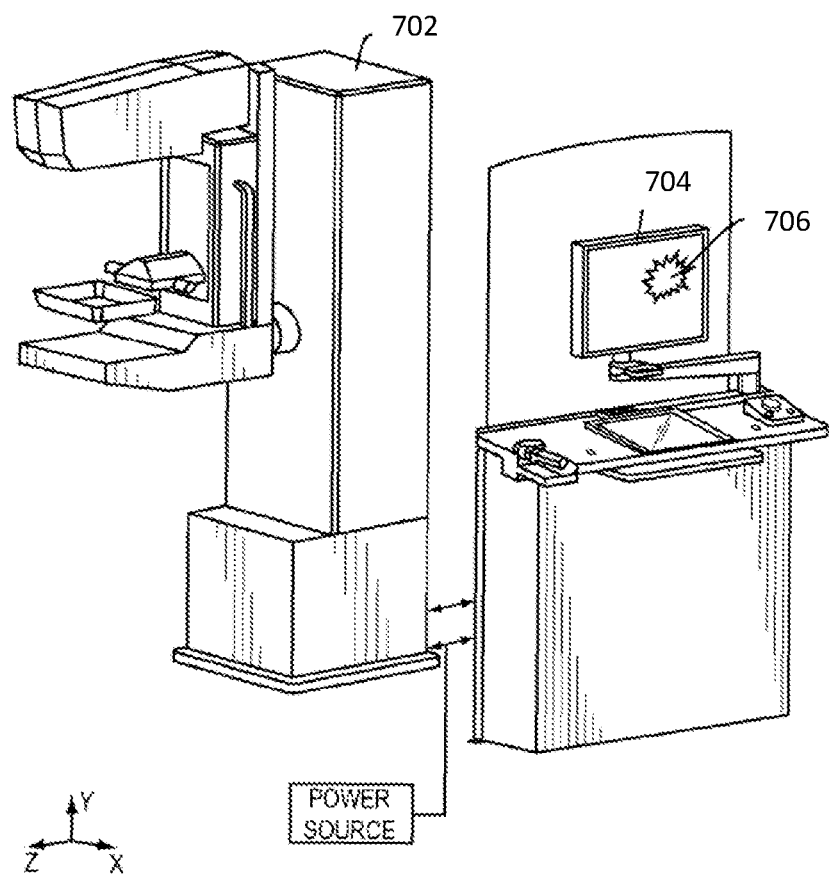
FIG. 7 depicts an example of a suitable tomosynthesis system in which one or more of the present embodiments may be implemented.

FIG. 7 depicts an example of a suitable tomosynthesis system 700 in which one or more of the present embodiments may be implemented. The tomosynthesis system 700 includes a gantry 702, a workstation 704 that is in communication with the gantry 702. The workstation may include a display that displays an indicator 706, such as a motion warning, or other information. The display of the workstation 704 may also be utilized for displaying and reviewing projection frames.

Figure 8:
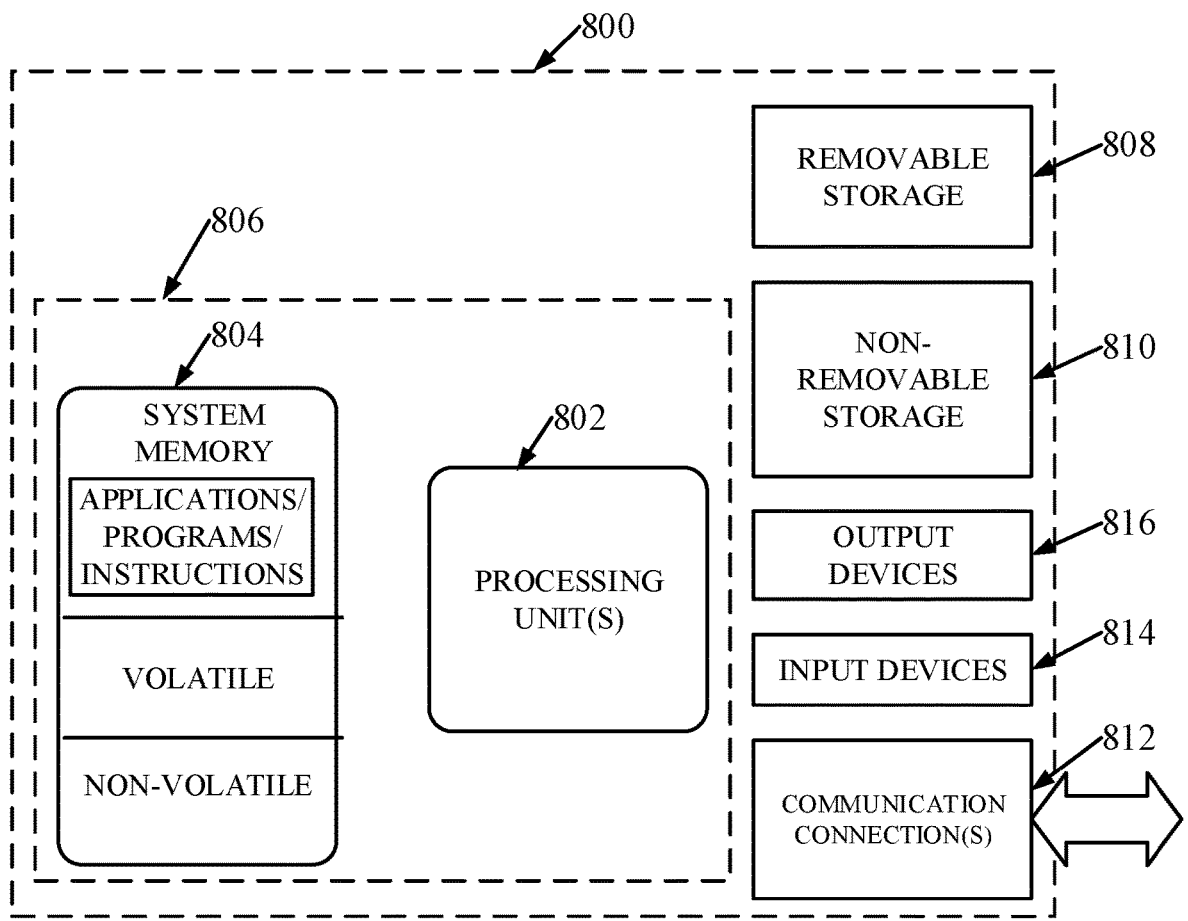
FIG. 8 depicts an example of a suitable operating environment in which one or more of the present embodiments may be implemented.

FIG. 8 depicts an example of a suitable operating environment 800 in which one or more of the present embodiments may be implemented. The example operating environment may be incorporated in the workstation 704 or other computing device that is being utilized to review medical images, such as the projection frames. In its most basic configuration, operating environment 800 typically includes at least one processing unit 802 and memory 804. The processing unit may be a processor, which is hardware. Depending on the exact configuration and type of computing device, memory 804 (storing, instructions to perform the motion detection techniques disclosed herein) may be volatile (such as RAM), non-volatile (such as ROM, flash memory, etc.), or some combination of the two. This most basic configuration is illustrated in FIG. 8 by dashed line 806. The memory 804 stores instructions that, when executed by the processing unit(s) 802, perform the methods and operations described herein. Further, environment 800 may also include storage devices (removable, 808, and/or non-removable, 810) including, but not limited to, magnetic or optical disks or tape. Similarly, environment 800 may also have input device(s) 814 such as keyboard, mouse, pen, voice input, etc. and/or output device(s) 816 such as a display, speakers, printer, etc. Also included in the environment may be one or more communication connections 812, such as LAN, WAN, point to point, etc. In embodiments, the connections may be operable to facility point-to-point communications, connection-oriented communications, connectionless communications, etc.

Operating environment 800 typically includes at least some form of computer readable media. Computer readable media can be any available media that can be accessed by processing unit 802 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media is non-transitory and does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 800 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are often available in medical offices, enterprise-wide computer networks, intranets and the Internet.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

This disclosure describes some embodiments of the present technology with reference to the accompanying drawings, in which only some of the possible embodiments were shown. For instance, while the present technology is primarily discussed with reference to the pectoral muscle, the technology may also be applied to other internal features of the breast with discernable or identifiable boundaries, such as implants or chest wall muscles in the image. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C. Further, one having skill in the art will understand the degree to which terms such as "about" or "substantially" convey in light of the measurements techniques utilized herein. To the extent such terms may not be clearly defined or understood by one having skill in the art, the term "about" shall mean plus or minus ten percent.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for identifying internal motion of a breast of a patient during an imaging procedure, the method comprising:
   compressing the breast of the patient in a mediolateral oblique (MLO) position;
   during compression of the breast, acquiring a first tomosynthesis MLO projection frame for a first angle with respect to the breast;
   during compression of the breast, acquiring a second tomosynthesis MLO projection frame for a second angle with respect to the breast;
   identifying a first boundary of a pectoral muscle in the first projection frame;
   generating a first representation of the first boundary of the pectoral muscle;
   identifying a second boundary of the pectoral muscle in the second projection frame;
   generating a second representation of the second boundary of the pectoral muscle;
   determining a difference between the first representation and the second representation; and
   generating a motion score based on at least the difference between the first representation and the second representation.

2. The method of claim 1, wherein the first generated representation is a two-dimensional representation.

3. The method of claim 1, wherein the difference is based on an area between the first representation and the second representation.

4. The method of claim 1, wherein the difference is based on a minimum distance between the first representation and the second representation.

5. The method of claim 1, further comprising:
   comparing the difference to an expected value, wherein the expected value is based on at least one of:
      an x-ray angle of an x-ray source for the first projection frame and an x-ray angle of the x-ray source for the second projection frame, or
      a fitted curve based on at least the first tomosynthesis MLO projection frame and the second tomosynthesis MLO projection frame; and
   based on the comparison of the difference to the expected value, generating a motion warning.

6. The method of claim 1, further comprising displaying at least a portion of the first projection frame and the second projection frame in a cine view concurrently with a plurality of parallel motion guides.

7. The method of claim 6, further comprising:
   receiving a selection of one of the plurality of the parallel motion guides;
   receiving an input to move the selected parallel motion guide to a new location; and
   based on the received input to move the selected parallel motion guide, displaying the selected parallel motion guide in the new location.

8. The method of claim 6, wherein the plurality of parallel motion guides are evenly spaced relative to one another.

9. A method for identifying internal motion of a breast of a patient during an imaging procedure, the method comprising:
   compressing the breast of the patient in a mediolateral oblique (MLO) position;
   acquiring a plurality of tomosynthesis MLO projection frames during the compressing of the breast, wherein the plurality of tomosynthesis MLO projection frames include an image of a portion of the breast and a portion of a pectoral muscle of the patient;
   for at least two of the plurality of the tomosynthesis MLO projection frames, identifying a boundary of the pectoral muscle;
   for the at least two of the plurality of the tomosynthesis MLO projection frames, generating a representation for the boundary of the pectoral muscle;
   determining a first difference between the generated representations for the at least two of the plurality of the tomosynthesis MLO projection frames;
   determining a second difference between the first difference and an expected value for the first difference;
   comparing the second difference to a predetermined threshold; and
   based on the comparison of the second difference to the predetermined threshold, generating a motion warning.

10. The method of claim 9, wherein the generated representation is a two-dimensional representation.

11. The method of claim 9, wherein the first difference is based on an area between the generated representations.

12. The method of claim 9, wherein the first difference is based on a minimum distance between the generated representations.

13. The method of claim 9, wherein the second difference is a shift variance value.

14. The method of claim 9, further comprising displaying at least a portion of the projection frames consecutively in a cine view concurrently with a plurality of parallel motion guides.

15. The method of claim 14, further comprising:
   receiving a selection of one of the plurality of the parallel motion guides;
   receiving an input to move the selected parallel motion guide to a new location; and
   based on the received input to move the selected parallel motion guide, displaying the selected parallel motion guide in the new location.

16. The method of claim 14, wherein the plurality of parallel motion guides are evenly spaced relative to one another.

17. A system for identifying internal motion of a breast of a patient during an imaging procedure, the system comprising:
   an x-ray source configured to move rotationally around the breast;
   a compression paddle configured to compress the breast in a mediolateral oblique (MLO) position;
   an x-ray detector disposed opposite the compression paddle from the x-ray source;
   at least one processor; and
   memory storing instructions that, when executed by the at least one processor, cause the system to perform a set of operations comprising:
      during a compression of the breast in the MLO position:
         emitting, from the x-ray source, a first x-ray emission from the x-ray source at a first angle relative to the breast;
         detecting, by the x-ray detector, the first x-ray emission from the x-ray source after the first x-ray emission has passed through the breast;

emitting, from the x-ray source, a second x-ray emission at a second angle relative to the breast; and detecting, by the x-ray detector, the second x-ray emission after the second x-ray emission has passed through the breast;

generating, based on the detected first x-ray emission, a first tomosynthesis MLO projection frame for the first angle;

generating, based on the detected second x-ray emission, a second tomosynthesis MLO projection frame for the second angle;

identifying a first boundary of a pectoral muscle in the first projection frame;

generating a first representation of the first boundary of the pectoral muscle;

identifying a second boundary of the pectoral muscle in the second projection frame;

generating a second representation of the second boundary of the pectoral muscle;

determining a difference between the first representation and the second representation; and generating a motion score based on at least the difference between the first representation and the second representation.

18. The system of claim 17, wherein the first generated representation is a two-dimensional representation.

19. The system of claim 17, wherein the difference is based on an area between the first representation and the second representation.

20. The system of claim 17, wherein the difference is based on a minimum distance between the first representation and the second representation.

21. A method for identifying internal motion of a breast of a patient during an imaging procedure, the method comprising:

compressing the breast of the patient;

acquiring a plurality of tomosynthesis projection frames during the compressing of the breast, wherein the plurality of tomosynthesis projection frames include an image of a portion of the breast and a portion of a pectoral muscle of the patient;

for at least a subset of the plurality of the tomosynthesis projection frames, identifying a boundary of the pectoral muscle;

for the identified boundaries of the pectoral muscle, generating a boundary representation for the identified boundary of the pectoral muscle;

generating a reference line that intersects the generated boundary representations;

identifying a reference point along the reference line;

for at least a subset of the generated boundary representations, calculating an intersection distance from the reference point to an intersection point of the respective boundary with the reference line;

determining expected intersection distance values based on the calculated intersection distances;

determining an intersection shift variance for each of the boundary representations for which an intersection distance is calculated;

comparing the intersection shift variance to a predetermined threshold; and based on the comparison of the intersection shift variance to the predetermined threshold, generating a motion warning.

* * * * *